(12) United States Patent
Dannhardt et al.

(10) Patent No.: US 8,957,103 B2
(45) Date of Patent: Feb. 17, 2015

(54) CONJUGATED 3-(INDOLYL)- AND 3-(AZAINDOLYL)-4-ARYLMALEIMIDE COMPOUNDS AND THEIR USE IN TUMOR TREATMENT

(75) Inventors: Gerd Dannhardt, Mainz (DE); Stanislav Plutizki, Mainz (DE); Christopher Ganser, Mainz (DE); Eva Lauermann, Mainz (DE)

(73) Assignee: Johannes Gutenberg—Universitat Mainz, Mainz (DE)

( * ) Notice: Subject to any disclaimer, the term of this patent is extended or adjusted under 35 U.S.C. 154(b) by 0 days.

(21) Appl. No.: 13/996,291

(22) PCT Filed: Dec. 15, 2011

(86) PCT No.: PCT/EP2011/072906
§ 371 (c)(1),
(2), (4) Date: Sep. 16, 2013

(87) PCT Pub. No.: WO2012/084683
PCT Pub. Date: Jun. 28, 2012

(65) Prior Publication Data
US 2013/0345281 A1 Dec. 26, 2013

(30) Foreign Application Priority Data
Dec. 23, 2010 (EP) ..................................... 10196865

(51) Int. Cl.
| C07D 403/04 | (2006.01) |
|---|---|
| A61K 31/4045 | (2006.01) |
| A61K 31/405 | (2006.01) |
| A61K 45/06 | (2006.01) |
| C07D 471/04 | (2006.01) |
| C07D 513/14 | (2006.01) |

(52) U.S. Cl.
CPC ............ C07D 403/04 (2013.01); C07D 471/04 (2013.01); C07D 513/14 (2013.01); A61K 31/4045 (2013.01); A61K 31/405 (2013.01); A61K 45/06 (2013.01)
USPC .......................................... 514/414; 548/466

(58) Field of Classification Search
None
See application file for complete search history.

(56) References Cited

U.S. PATENT DOCUMENTS

| 5,057,614 | A | 10/1991 | Davis et al. |
|---|---|---|---|
| 5,721,245 | A | 2/1998 | Davis et al. |
| 8,008,320 | B2 | 8/2011 | Dannhardt |
| 8,841,319 | B2 | 9/2014 | Dannhardt |
| 2013/0029986 | A1 | 1/2013 | Dannhardt |
| 2013/0131060 | A1* | 5/2013 | Dannhardt et al. ........ 514/235.2 |

FOREIGN PATENT DOCUMENTS

| CA | 2010636 | | 12/1999 |
|---|---|---|---|
| EP | 0328026 | A1 | 8/1989 |
| EP | 0384349 | A1 | 8/1990 |
| EP | 0540956 | A1 | 5/1993 |
| EP | 1224932 | A1 | 7/2002 |
| EP | 1845094 | A1 | 10/2007 |
| WO | WO 91/13071 | A1 | 9/1991 |
| WO | WO 95/07910 | A1 | 3/1995 |
| WO | WO 97/34890 | A1 | 9/1997 |
| WO | WO 00/21927 | A2 | 4/2000 |
| WO | WO 00/38675 | A1 | 7/2000 |
| WO | WO 02/10158 | A2 | 2/2002 |
| WO | WO 02/38561 | A1 | 5/2002 |
| WO | WO 03/057202 | A1 | 7/2003 |
| WO | WO 03/095452 | A1 | 11/2003 |
| WO | WO 03/103663 | A2 | 12/2003 |
| WO | WO 2006/006939 | A1 | 1/2006 |
| WO | WO 2006/061212 | A1 | 6/2006 |
| WO | WO 2009/071620 | A1 | 6/2009 |

OTHER PUBLICATIONS

Patent Cooperation Treaty, International Searching Authority, Search Report and Written Opinion for PCT/EP2011/072906, 8 pages, Mar. 9, 2012.
Peifer et al., "Design, Synthesis, and Biological Evaluation of 3,4-Diarylmaleidides as Angiogenesis Inhibitors", J. Med. Chem., 49, 1271-1281 (2006).
Peifer et al., "Profile and Molecular Modeling of 3-(Indole-3-yl)-4-(3,4,5-trimethoxyphenyl)1H-pyrrole-2,5-dione (1) as a Highly Selective VEGF-R2/3 Inhibitor", J. Med. Chem., 49, 7549-7553 (2006).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEFG-R) Inhibitors", J. Med. Chem., 51, 3814-3824 (2008).
Zhang et al., "3-(7-Azaindolyl)-4-arylmaleimides as potent, selective inhibitors of glycogen synthase kinase-3", Bioorganic & Medicinal Chemistry Letters 14, 3245-3250 (2004).

* cited by examiner

Primary Examiner — Timothy R Rozof
(74) Attorney, Agent, or Firm — Viksnins Harris & Padys PLLP

(57) ABSTRACT

The present invention relates to 3-(Indolyl)- and 3-(azaindolyl)-4-phenylmaleimide compounds of formula (I) wherein $R^1$, $R^2$ and $R^3$ are as defined in the description, and the physiologically acceptable salts, solvates and solvates of the salts of the compounds of formula (I). The compounds of formula (I) are suitable for treating tumors.

(I)

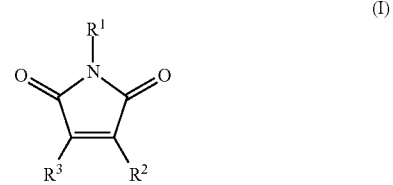

16 Claims, No Drawings

CONJUGATED 3-(INDOLYL)- AND 3-(AZAINDOLYL)-4-ARYLMALEIMIDE COMPOUNDS AND THEIR USE IN TUMOR TREATMENT

The present invention relates to 3-(indolyl)- and 3-(azaindolyl)-4-arylmaleimide compounds, pharmaceutical compositions containing them, and their use in tumor treatment.

Cancer is currently one of the most frequent causes of death in industrialized countries, and gastrointestinal carcinomas are among the most common types of cancer. There is, however, still no causal therapy available. Standard therapy of colorectal cancer basically consists of primary surgical resection and adjuvant cytotoxic chemotherapy involving agents such as 5-fluorouracil (5-FU), leucovorin, capecitabine, irinotecan, bevacizumab, cetuximab and oxiplatin. Radical surgery represents the standard form of curative gastric cancer therapy and is in general accompanied by treatment with chemotherapeutics such as 5-FU, leucovorin, epirubicin, docetaxel, cisplatin and sometimes also concurrent radiation therapy. As these methods can severely impair a patient's quality of life there is strong interest in advances in therapy: In particular attention is focused on achieving a high target cell selectivity of cancer treatment and on overcoming escape mechanisms such as the development of drug resistances which often occur by the accumulation of mutations in rapidly dividing cancer cells.

A physiological process often focused on in development of anti-cancer agents is apoptosis, a controlled form of cell death eliminating damaged, aberrant, infected, old or superfluous cells. In particular mucosa tissue such as gastrointestinal mucosa is characterized by a rapid epithelial cell turnover in which homeostasis is maintained predominantly by apoptosis. In the course of cancer development the capability of cells to undergo apoptosis is usually reduced, i.e. cancer cells are not or less susceptible to apoptotic signals. Agents that are able to promote readiness of apoptosis or induce apoptosis in cancer cells (pro-apoptotic agents) may therefore be useful for prevention and/or therapy of cancer, including colorectal or gastric adenocarcinoma. In fact, when treating cancer it is desirable to avoid violent destruction of cancer cells which will lead to "unclean" necrotic cell death including the release of cell contents and fragments into the extracellular environment, thus promoting inflammation and other undesirable side effects. It is therefore preferable to induce the less noxious programmed cell death (apoptosis). This physiological process leads to an orderly self-destruction without the release of toxins or pro-inflammatory substances into the surrounding tissue. The application of pro-apoptotic agents is therefore an attractive means to achieve a less injurious removal of cancer cells or to increase their sensitivity to conventional treatments, which would allow to reduce both dosage (and thus systemic side effects) and secondary effects caused by necrotic cell death.

One essential prerequisite for growth and metastasis of cancers which form tumors is angiogenesis, a process involving the formation of new blood vessels from pre-existing capillary endothelial cells. When reaching a certain size, generally about 3 mm$^3$, further growth of a cluster of cancer cells becomes completely dependent on angiogenesis which is required for supplying the cells with oxygen and other essential nutrients and probably also for removing their metabolic waste. Cells breaking away from an established tumor may enter the blood vessel and be carried to a distant site to start a secondary tumor there (metastasis). Tumor cells may enhance angiogenesis by overexpression of pro-angiogenic factors, e.g. VEGF, FGF2, PDGF and interleukins, but also by down-regulation of inhibitory factors, e.g. thrombospondin. In general, this is especially pronounced with tumors having a high microvessel density as well as a particular aggressive behavior and high tendency to metastasize. Therefore, inhibitors of angiogenesis are researched as antitumor agents.

Protein kinases are an interesting class of target molecules for developing improved cancer therapies. These proteins are known to regulate the majority of cellular pathways including such relevant for control cell growth, cell movement, apoptosis resistance and survival—all processes relevant for cancer growth and progression. In fact, the tyrosine kinases act primarily as growth factor receptors. Deregulation of protein kinases is a frequent cause of diseases, in particular cancer. Some protein kinase inhibitors including monoclonal antibodies such as trastuzumab, cetuximab, panitumumab, rituximab and bevacizumab as well as small molecules such as imatinib, gefitinib, erlotinib, sorafenib and sunitinib are therefore useful for treating cancer. Despite these first achievements, many tumors are still treatment resistant.

Moguntinones, a class of small molecule compounds developed at the Johannes Gutenberg University Mainz comprise 3-(indolyl)- or 3-(azaindolyl)-4-arylmaleimide derivatives with tumor and vascular targeting properties.

WO 2006/061212 describes 3-(indolyl)- or 3-(azaindolyl)-4-arylmaleimide derivatives which are angiogenesis inhibitors and proposes their use for controlling angiogenesis and/or vascular dysfunction.

The use of certain 3-(indolyl)- or 3-(azaindolyl)-4-arylmaleimide derivatives showing an inhibitory effect on the protein kinase FTL3 for treatment and prevention of leukemia is described in WO 2009/071620.

WO 02/38561 describes kinase inhibitors of the formula

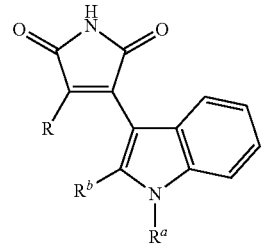

wherein R is an aryl residue such as a hydroxyl substituted phenyl group.

Compounds of similar structure and having a comparable effect or other pharmacological activity are described in EP 328 026 A, WO 02/10158, WO 03/057202, WO 03/095452, WO 03/103663, WO 95/07910, WO 00/38675, WO 97/34890, WO 91/13071, EP 384 349 A, EP 540 956, EP 1 224 932 A, WO 00/021927, and Bioorganic & Medicinal Chemistry Letters 14 (2004), 3245-3250.

EP 1 845 094 A and WO 2006/06939 describe the kinase inhibitor of formula:

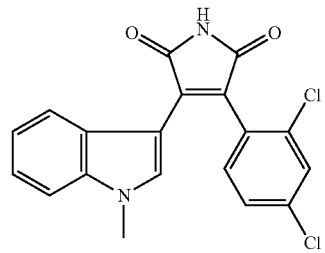 [SMILES: Cn1cc(C2=C(c3ccc(Cl)cc3Cl)C(=O)NC2=O)c2ccccc21]

and related compounds for use in treating cancer.

The publications of Peifer et al. in J. Med. Chem. 2006, 49: 1271-1281; J. Med. Chem. 2006, 49: 7549-7553; and J. Med. Chem. 2008, 51: 3814-3824 are concerned with the design, synthesis and evaluation of 3,4-diarylmaleimides as angiogenesis inhibitors.

The present invention relates to compounds of formula I:

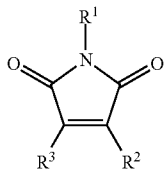
(I)

wherein
$R^1$ is —H, $C_1$-$C_6$-alkyl, phenyl-$C_1$-$C_4$-alkyl or phenyl and is preferably —H;
$R^2$ is a phenyl group which is substituted with 2 or 3 $C_1$-$C_6$-alkoxy groups and is preferably a group of formula:

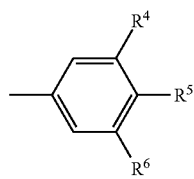

wherein $R^4$, $R^5$ and $R^6$ are $C_1$-$C_6$-alkoxy;
$R^3$ is selected from:

a)
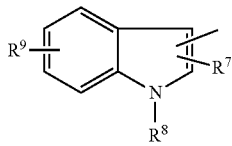

b)
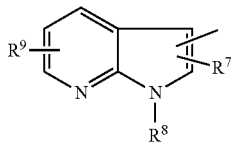

c)
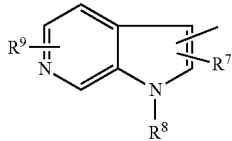

d)
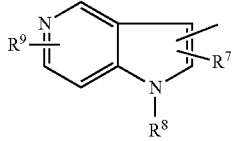

e)
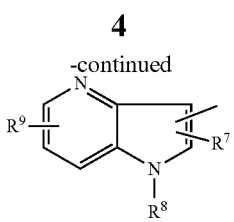

wherein
$R^7$ is —H, $C_1$-$C_6$-alkyl or phenyl, and is preferably —H;
$R^9$ is —H, $C_1$-$C_6$-alkoxy, —OH, halogen, —NH$_2$, $C_1$-$C_6$-alkylamino, alkylamino, 5- or 6-membered heteroaryl, or 5- or 6-membered heterocyclyl, and is preferably —H, $C_1$-$C_6$-alkyl or halogen; and
$R^8$ is —$C_1$-$C_8$-alkyl-$X^1$—$X^2$—$R^{10}$, —$C_2$-$C_8$-alkenyl-$X^1$—$X^2$—$R^{10}$ or —$C_2$-$C_8$-alkynyl-$X^1$—$X^2$—$R^{10}$, and is preferably —$C_1$-$C_8$-alkyl-$X^1$—$X^2$—$R^{10}$, wherein;
$X^1$ is a single bond, —(OCH$_2$CH$_2$)$_n$—, or —(OCH$_2$CH$_2$CH$_2$)$_n$—, wherein n is 1, 2 or 3, and is preferably a single bond;
$X^2$ is —OC(O)—, —NR$^{11}$C(O)—, —C(O)O—, —C(O)NR$^{11}$—, —OC(O)NR$^{11}$—, —NR$^{11}$C(O)O—, —NR$^{12}$C(O)NR$^{12}$—, —OS(O)$_2$—, —S(O)$_2$O—, —OS(O)$_2$O—, —NR$^{11}$—, —O—, —S—, or

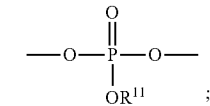
;

$R^{10}$ is selected from
a) linear or branched $C_1$-$C_6$-alkyl substituted with one residue selected from —NHR$^{11}$, —OH, —SH, —C(O)OH and —S(O)$_2$OH, and optionally further substituted with one, two or three residues independently selected from —NHR$^{13}$, —OH, —SR$^{13}$, —C(O)OH, —S(O)$_2$OH, —C(O)NH$_2$, —NHC(NH)NH$_2$, —NHC(O)NH$_2$, $C_3$-$C_7$-cycloalkyl, aryl, in particular phenyl, and 5- or 6-membered heteroaryl, in particular indolyl or imidazolyl, said cycloalkyl being optionally being substituted with one or two $C_1$-$C_6$-alkyl, and said aryl and heteroaryl being optionally substituted with one, two, three or four substituents independently selected from —OH, $C_1$-$C_6$-alkyl and —C(O)OH;
b) a 5- or 6-membered saturated heterocyclyl, in particular pyrrolidinyl, optionally substituted with one, two or three substituents independently selected from $C_1$-$C_6$-alkyl, —OH and —C(O)OH;
c) $C_1$-$C_6$-alkyl substituted with monocyclic or bicyclic heteroaryl, in particular with imidazolyl such as 5-imidazolyl, said heteroaryl being optionally substituted with one, two, three or four substituents independently selected from —OH, $C_1$-$C_6$-alkyl and —C(O)OH;
d) monocyclic or bicyclic aryl, optionally substituted with one, two, three or four substituents independently selected from —OH, $C_1$-$C_6$-alkyl and —C(O)OH;
e) $C_3$-$C_7$-cycloalkyl optionally substituted with one or two $C_1$-$C_6$-alkyl;
f) monocyclic or bicyclic heteroaryl, optionally substituted with one, two, three or four substituents independently selected from —OH, $C_1$-$C_6$-alkyl, and —C(O)OH;
g) $C_1$-$C_6$-alkyl substituted with monocyclic or bicyclic aryl, in particular with phenyl, said aryl being optionally substituted with one, two or three substituents independently selected from —OH, $C_1$-$C_6$-alkyl, and —C(O)OH; and h) —(CH₂CH₂O)ₘH, —(CH(CH₃)CH₂O)ₘH, or —(CH₂CH(CH₃)O)ₘH, wherein m is 1 to 10;
R$^{11}$ is selected from —H, C$_1$-C$_8$-alkyl, phenyl and benzyl;
R$^{12}$ is —H or C$_1$-C$_8$-alkyl; and
R$^{13}$ is selected from —H, C$_1$-C$_8$-alkyl, phenyl and benzyl;
and the physiologically acceptable salts, solvates and solvates of the salts of the compounds of formula I.

The term "alkyl", "alkoxy", "alkylamino", "alkylene" etc. includes linear or branched alkyl or alkylene groups having 1 to 8, in particular 1 to 6 and preferably 1 to 4 carbon atoms. Examples for alkyl groups are methyl, ethyl, n-propyl, i-propyl, n-butyl, sec-butyl, iso-butyl, t-butyl, n-pentyl or n-hexyl. Examples for alkoxy groups are methoxy, ethoxy, n-propoxy, isopropoxy, n-butoxy. Examples for alkylene groups are methylene, ethylene, n-propylene, isopropylene, n-butylene, isobutylene etc.

The term "alkenyl" includes linear or branched alkenyl groups, i.e. hydrocarbon chains containing at least one double bond, having 2 to 8, in particular 2 to 6 and preferably 2 to 4 carbon atoms. Examples for alkenyl groups are vinyl and allyl.

The term "alkynyl" includes linear or branched alkynyl groups, i.e. hydrocarbon chains containing at least one triple bond, having 2 to 8, in particular 2 to 6 and preferably 2 to 4 carbon atoms. Examples for alkynyl groups are ethynyl and propargyl.

Halogen means F, Cl, Br and I, preferably F and Cl.

The term "cycloalkyl" includes optionally substituted, non-aromatic saturated monocyclic C$_3$-C$_7$- and bicyclic C$_9$-C$_{11}$-hydrocarbon groups. Thus, a cycloalkyl described herein may be a C$_3$-C$_7$-monocyclic cycloalkyl.

The term "aryl" refers to optionally substituted, aromatic monocyclic or bicyclic C$_6$-C$_{12}$-hydrocarbonyl groups which may be fused to 5- or 6-membered heterocyclyl or heteroaryl. Preferably, "aryl" is optionally substituted phenyl.

The term "heterocyclyl" denotes an optionally substituted cycloalkyl group, wherein at least one carbon ring atom has been replaced by O, N or S. Thus, a heterocycyl described herein may have 5 or 6 ring atoms (i.e. is a 5- or 6-membered heterocyclyl) containing one or two heteroatoms which are independently selected from O, N, and S. Heterocyclyl groups may be bound via a carbon atom (C-bound) or a nitrogen atom (N-bound). Examples for "heterocyclyl" are pyrrolidinyl, tetrahydrofuranyl, imidazolidinyl, piperidinyl, morpholinyl, thiomorpholinyl and piperazinyl. If heterocyclyl is substituted, the substituent may be at a carbon or at a nitrogen ring atom.

The term "heteroaryl" denotes an optionally substituted monocyclic or bicyclic aryl group, wherein at least one carbon ring atom has been replaced by O, N or S. Thus, a heteroaryl may be monocyclic with 5 or 6 ring atoms (i.e. is a 5- or 6-membered heteroaryl) containing one or two heteroatoms which are independently selected from O, N, and S or bicyclic with 9 or 10 ring atoms (i.e. is a 9- or 10-membered heteroaryl) containing one, two or three heteroatoms which are independently selected from O, N, and S. Heteroaryl groups may be bound via a carbon atom (C-bound) or a nitrogen atom (N-bound). Examples for "heteroaryl" are indolyl, imidazolyl, azaindolyl, pyrrolyl, quinolinyl, isoquinolinyl, oxazolyl, thiazolyl and pyrimidinyl. If heteroaryl is substituted, the substituent may be at a carbon or at a nitrogen ring atom.

Examples of substituents comprised by said C$_3$-C$_7$-cycloalkyl, aryl, heterocyclyl and heteroaryl groups are —OH, —NH$_2$ and —SH.

Physiologically acceptable salts of the compounds of formula I include acid addition salts with physiologically acceptable acids. Examples of suitable physiologically acceptable organic and inorganic acids are hydrochloric acid, hydrobromic acid, phosphoric acid, sulfuric acid, C$_1$-C$_4$-alkylsulfonic acids, such as methanesulfonic acid, cycloaliphatic sulfonic acids, such as S-(+)-10-camphor sulfonic acid, aromatic sulfonic acids, such as benzene sulfonic acid and toluene sulfonic acid, carboxylic acids, such as acetic acid, and hydroxycarboxylic acids, such as oxalic acid, malonic acid, maleic acid, mandelic acid, ascorbic acid, fumaric acid, gluconic acid, lactic acid, tartaric acid, citric acid, glycolic acid, adipic acid and benzoic acid. Other utilizable acids are described, e.g., in "Fortschritte der Arzneimittelforschung" [Advances in drug research], Volume 10, pages 224 ff., Birkhäuser Verlag, Basel and Stuttgart, 1966.

Physiologically acceptable salts of the compounds of formula I include also base addition salts with inorganic bases, such as alkali metal hydroxides, like sodium or potassium hydroxide, alkaline earth metal hydroxides, like magnesium or calcium hydroxide; ammonium salts, or salts with organic bases such as tetramethylammonium hydroxide, triethylamine, tri(hydroxyethyl)amine, lysine, arginine or histidine.

The physiologically acceptable salts of the compounds of formula I also include salts of a physiologically tolerated anion, e.g. a deprotonated physiologically acceptable acid, with a compound of formula I, wherein one or more than one nitrogen atom may be quaternized, e.g. with an alkyl residue (e.g. methyl or ethyl).

Physiologically acceptable solvates are in particular hydrates.

According to one embodiment, the compounds of formula I are compounds
(a) having formula Ia:

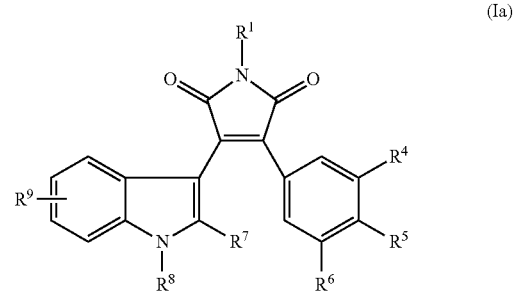

(Ia)

wherein R$^1$, R$^7$, R$^8$ and R$^9$ are as defined above and R$^4$, R$^5$ and R$^6$ are C$_1$-C$_6$-alkoxy;
(b) having formula Ib:

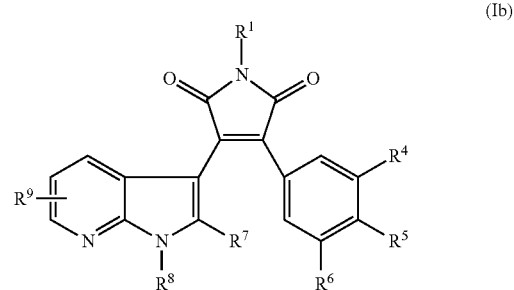

(Ib)

wherein R$^1$, R$^7$, R$^8$ and R$^9$ are as defined above and R$^4$, R$^5$ and R$^6$ are C$_1$-C$_6$-alkoxy;

(c) having formula Ic:

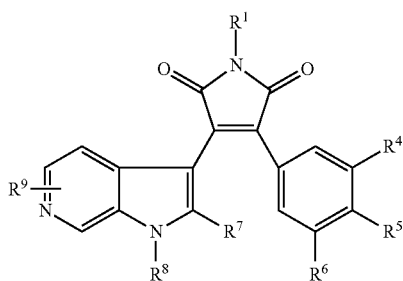

wherein $R^1$, $R^7$, $R^8$ and $R^9$ are as defined above and $R^4$, $R^5$ and $R^6$ are $C_1$-$C_6$-alkoxy;

(d) having formula Id:

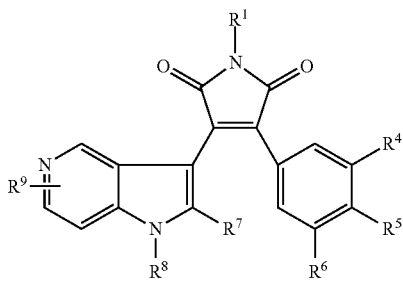

wherein $R^1$, $R^7$, $R^8$ and $R^9$ are as defined above and $R^4$, $R^5$ and $R^6$ are $C_1$-$C_6$-alkoxy; or (e) having formula Ie:

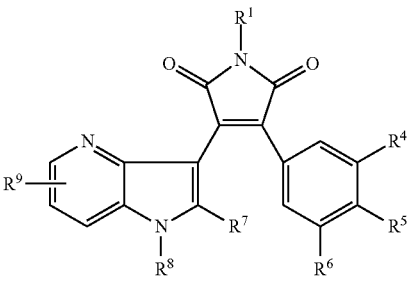

wherein $R^1$, $R^7$, $R^8$ and $R^9$ are as defined above and $R^4$, $R^5$ and $R^6$ are $C_1$-$C_6$-alkoxy.

According to a further embodiment, $R^8$ is —$C_1$-$C_8$-alkyl-$X^1$—OC(O)—$R^{10}$, —$C_1$-$C_8$-alkyl-$X^1$—$NR^{11}$C(O)—$R^{10}$, —$C_1$-$C_8$-alkyl-$X^1$—C(O)$NR^{11}$—$R^{10}$, —$C_1$-$C_8$-alkyl-$X^1$—OC(O)$NR^{11}$—$R^{10}$ or —$C_1$-$C_8$-alkyl-$X^1$—$NR^{12}$C(O)$NR^{12}$—$R^{10}$.

According to a further embodiment, $R^1$, $R^7$ and $R^9$ are —H.

According to a further embodiment, $R^{10}$ is linear or branched $C_1$-$C_8$-alkyl substituted with one —$NHR^{11}$, and optionally further substituted with one, two or three substituents independently selected from —$NHR^{13}$, —OH, —$SR^{13}$, —C(O)OH, —S(O)$_2$OH, —C(O)$NH_2$, —NHN(H)$NH_2$, $C_3$-$C_7$-cycloalkyl, aryl, in particular phenyl, and 5- or 6-membered heteroaryl, in particular indolyl or imidazolyl, said cycloalkyl optionally being substituted with one or two $C_1$-$C_8$-alkyl, and said aryl and heteroaryl being optionally substituted with one, two, three or four substituents independently selected from —OH, $C_1$-$C_6$-alkyl, and —C(O)OH.

According to an alternative embodiment, $R^{10}$ is —(CH$_2$CH$_2$O)$_m$H, —(CH(CH$_3$)CH$_2$O)$_m$H, or —(CH$_2$CH(CH$_3$)O)$_m$H, and m is 1 to 10.

According to a further alternative embodiment, —$X^2$—$R^{10}$ is a biogenic amine, i.e. a primary amine derived from a naturally occurring amino acid by decarboxylation (removal of C1 carboxy group), that is coupled to $X^1$ by an amide bond ($X^1$—C(O)$NR^{11}$—), an urethane bond ($X^1$—OC(O)$NR^{11}$—) or an urea bond ($X^1$—$NR^{12}$C(O)$NR^{12}$—), preferably involving its α-amino group. In a preferred embodiment, the biogenic amine is histamine.

According to a further preferred embodiment, $X^2$—$R^{10}$ is a naturally occurring amino acid, in particular an L-α-amino acid, or a stereoisomer thereof, coupled to $X^1$ by an ester bond ($X^1$—OC(O)—) or an amide bond ($X^1$—$NR^{11}$C(O)—), preferably involving its C1 carbonyl group; or coupled to $X^1$ by an amide bond ($X^1$—C(O)$NR^{11}$—), an urethane bond ($X^1$—OC(O)$NR^{11}$—) or an urea bond ($X^1$—$NR^{12}$C(O)$NR^{12}$—), preferably involving its α-amino group. The naturally occurring amino acid may be selected from isoleucine, alanine, leucine, asparagine, lysine, aspartic acid, methionine, cysteine, phenylalanine, histidine, tryptophan, proline, glutamic acid, threonine, glutamine, glycine, valine, serine, tyrosine, arginine, ornithine and citrulline.

Exemplary compounds of formula I are

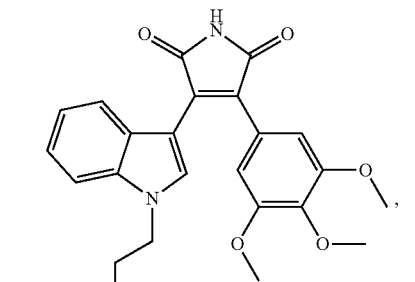

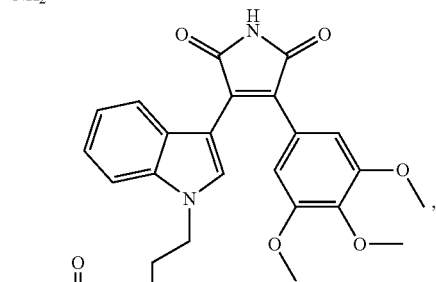

-continued

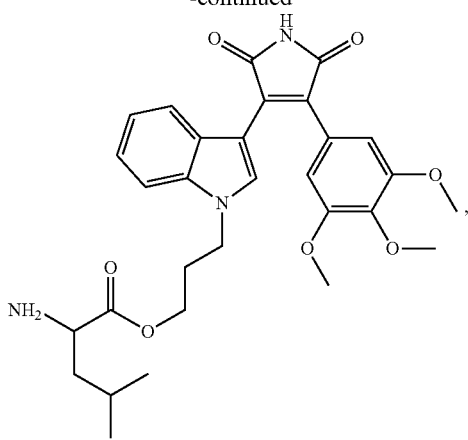

,

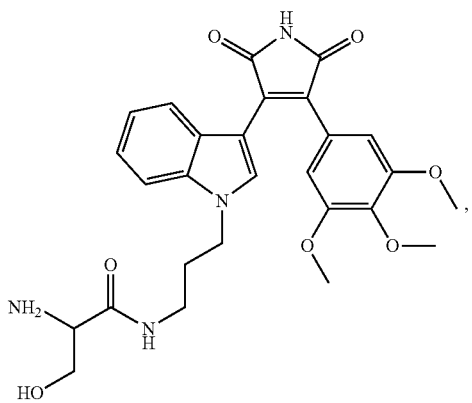

,

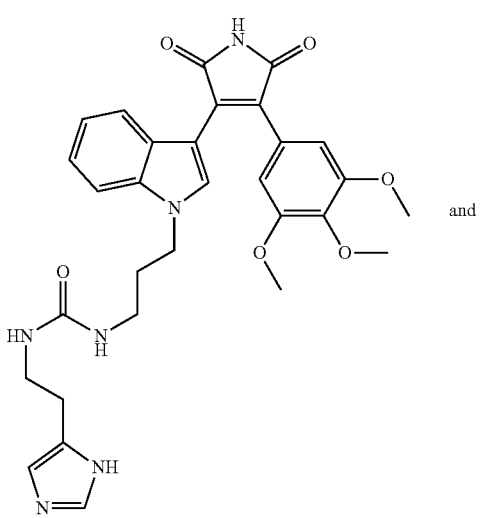

and

-continued

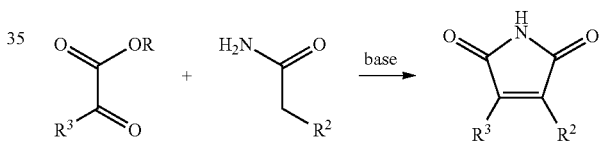

;

and the physiologically acceptable salts, solvates and solvates of the salts thereof.

The compounds of the present invention can be prepared according to known methods, for example according to the methods, which are disclosed in WO 02/38561, EP 328 026, WO 03/095452, WO 03/103663 and WO 2006/061212. For the purposes of the present invention a modified procedure reported in *Tetrahedron Letters* (1999) 40: 1109-1112 has been proven to be particularly efficient. This procedure can be illustrated by the following reaction sequence:

An indole glyoxyl ester is reacted with a phenyl acetamide derivative in a one-pot reaction in an inert solvent in the presence of a strong base. Preferably an ether is used as an inert solvent, such as tetrahydrofurane or dioxane. As a base potassium tert.-butoxide can for example be used. The water formed during the reaction is removed, for example by using a molecular sieve. The phenyl acetamides used as starting material are readily available from the corresponding acetic acids which are converted to the acid chloride and hydrolyzed with ammonia. The indole glyoxyl esters (R=methyl, ethyl) can be synthesized by Friedel-Crafts-type acylation of the corresponding indole derivative with methyl or ethyl oxalyl chloride, cf. *Tetrahedron* 1999, 55 (43), 12577-12594. The corresponding azaindole glyoxyl esters can be prepared according to the method reported in J. Org. Chem. 2002, 67: 6226-6227 or by Friedel-Crafts acylation in the presence of aluminum chloride, cf. Organic Letters (2000) vol. 2, no. 10, 1485-1487. The 4- and 6-azaindole starting compounds can be prepared by reacting 2-chloro-3-nitropyridine or 3-nitro-4-chloropyridine with vinyl magnesium bromide to give the 7-chloro-substituted 4- or 6-azaindole. The chloro substituent is then removed by catalytic hydrogenation. Said reactions are carried out as described in J. Org. Chem. 67: 2345-2347 (2002) and J. Heterocycl. Chem. 29: 359-363 (1992). The 4-aza-indole starting compound can also be synthesized according to the procedures disclosed in Org. Biomol. Chem. 3, 20, 3701-3706 (2005).

The 5- and 7-azaindole starting compounds can be prepared by reacting 2- or 4-aminopyridine with di-tert.-butyl-dicarbonate to 2- or 4-t-butoxycarbonylaminopyridine which is then reacted with methyl iodide and dimethylformamide in the presence of t-butyl lithium. The obtained product is then treated with a strong acid to give 5- or 7-azaindole. Said reactions are described in *Synthesis* 7, 877-882 (1996).

The compounds of the present invention have antineoplastic activity and can therefore be used for the treatment or prevention of tumors, in particular solid tumors, such as astrocytoma, bladder cancer, bone cancer, brain tumor, breast cancer, bronchial tumor, cervical cancer, colorectal cancer, endometrial cancer, esophageal cancer, gallbladder cancer, gastrointestinal stromal tumor, germ cell tumor, glioma, head and neck cancer, liver cancer, lymphoma, sarcoma, lung cancer, melanoma, ovarian cancer, pancreatic cancer, thyroid cancer, neuroblastoma, prostate cancer, renal cancer, skin cancer, squamous neck cancer, stomach (gastric) cancer, testicular cancer. The compounds of the invention are especially useful for treatment or prevention of cervical cancer, colorectal cancer, gastrointestinal stromal tumor, liver cancer, lung cancer, ovarian cancer, prostate cancer, stomach cancer, and pancreatic carcinoma.

According to a further embodiment, the compounds of the present invention can be used for the treatment or prevention of leukemia. Leukemia according to the present invention comprises in particular acute lymphocytic leukemia (also known as acute lymphoblastic leukemia, or ALL), acute myelogenous leukemia (also known as acute myeloid leukemia, or AML); chronic lymphocytic leukemia (CLL), mixed-lineage leukemia and chronic myelogenous leukemia (CML). These leukemias and further subtypes of these leukemias are defined by morphological, histochemical and immunological techniques that are well known by those skilled in the art.

In a further embodiment, the invention relates to the treatment of AML or ALL.

In a further embodiment of the invention, the leukemia is characterized by leukemic cells which are positive for expression of FLT3. In a particular embodiment of the invention, the leukemia is characterized by leukemic cells which show enhanced expression of FLT3, compared to non-malignant cells of the same cell type.

A further embodiment of the invention is a combination of the compounds of the present invention with one or more than one chemotherapeutic agent including antineoplastic agents, multidrug resistance reversing agents; and biological response modifiers, and combinations thereof, examples being given below.

Suitable antineoplastic agents may be selected from the group comprising compounds affecting integrity and synthesis of DNA, e.g. topoisomerase I inhibitors; alkylating agents: intercalating agents or DNA-binding antibiotics; antimitotic compounds such as taxanes: vinca alkaloids or colchicine derivatives; compounds for targeted cancer therapy such as protein kinase inhibitors, antibodies binding to cell membrane receptors and soluble decoy receptors; compounds affecting the cell metabolism, e.g. farnesyltransferase inhibitors, purine or pyrimidine analogues.

Examples for antineoplastic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib.

Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, axitinib, neratinib, vatalanib, pazopanib, midostaurin and enzastaurin.

Examples for antineoplastic agents which are antibodies comprise trastuzumab, cetuximab, panitumumab, rituximab, bevacizumab, mapatumumab, conatumumab, lexatumumab and the like.

An example for a multidrug resistance reversing agent is PSC 833, a potent inhibitor of the efflux of antitumor drugs mediated by P-glycoprotein.

Suitable biological response modifiers may be selected from the group consisting of monoclonal antibodies and cytokines, such as interferons, interleukins and colony-stimulating factors, e.g., rituxan, CMA-676, interferon-alpha recombinant, interleukin-2, interleukin-3, erythropoetin, epoetin, G-CSF, GM-CSF, filgrastim, sargramostim and thrombopoietin.

According to a particular embodiment, the further chemotherapeutic agent is a topoisomerase I inhibitor and especially camptothecin or a derivative thereof such as described by Pommier, Y. (2006), Nature Reviews Cancer 6: 789-802. Examples for topomerase I inhibitors comprise compounds such as irinotecan (in particular irinotecan hydrochloride), topotecan (in particular topotecan hydrochloride), rubitecan, exatecan (in particular exatecan mesylate), lurtotecan, gimatecan, prothecan, karenitecin, belotecan (in particular belotecan hydrochloride), silatecan or diflomotecan and the salts thereof.

The weight ratio of the compounds of the invention to the chemotherapeutic agent is in general in the range from 5:1 to 1:500, in particular 3:1 to 1:200.

The combination of the invention exhibits enhanced tumor activity.

A further embodiment of the invention is a pharmaceutical composition comprising at least one compound of formula I with an additional chemotherapeutic agent as defined above. In general, the pharmaceutical compositions comprise an amount therapeutically effective for tumor treatment of at least one compound of formula I as defined herein. Said at least one compound of formula I may be a compound of formula Ia, Ib, Ic or Id as defined herein or a combination thereof.

A further embodiment of the invention is a compound of formula I for use in a method of treating tumors.

According to a further embodiment, said method comprises the use of an additional therapeutic agent (other than a compound of formula I). The additional therapeutic agent may be as defined above.

For use the compounds or combinations of the present invention can be incorporated into standard pharmaceutical dosage forms. For example, the compounds or combinations are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elixirs. Pharmaceutical excipients and adjuvants which can be added to include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers.

The therapeutically effective amount of a compound of formula I as defined may be administered systemically to said mammal, wherein said systemic administration comprises: (1) injection or infusion into suitable body tissues or cavities of a pharmaceutical composition containing said compound or combination in suitable liquid form such as aqueous solutions, emulsions or suspensions for intraarterial, intra- or transdermal (including subcutaneous) and most commonly intramuscular or intravenous delivery thereof; or for serving as a depot for delivery thereof; (2) instillation into suitable body tissues or cavities of a pharmaceutical composition containing said compound or combination in suitable solid form, e.g., comprising a matrix of bio-compatible and bio-erodible materials in which particles of at least one compound of formula I are dispersed for serving as a solid implant composition for delayed-, sustained-, and/or controlled-release delivery thereof; or (3) ingestion or administration of a pharmaceutical composition containing said compound or combination in suitable solid or liquid form for transdermal delivery thereof, for instance a transdermal patch or a subepidermal (subcuticular) implant, for peroral delivery thereof.

The dosage forms described herein may be formulated so as to provide controlled-, sustained-, and/or delayed release of the active ingredient from said dosage form.

Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated. Tablets and capsules are preferred dosage forms.

Said therapeutically effective amount of a compound of formula I as defined may also be administered locally to said mammal, wherein said local administration comprises: (1) injection or infusion into a local site affected with abnormal angiogenesis and/or vascular dysfunction of a pharmaceutical composition containing said compound of formula I or combination in suitable liquid form for delivery thereof, including components which provide delayed-release, controlled-release, and/or sustained-release of said compound or combination into said local site; or for serving as a depot for delivery thereof wherein said composition provides storage of said compound or combination and thereafter delayed-, sustained-, and/or controlled-release thereof; or (2) instillation of a pharmaceutical composition containing said compound or combination in suitable solid form for serving as a solid implant for delivery thereof, said composition optionally providing delayed-, sustained-, and/or controlled-release of said compound or combination to said local site.

The therapeutically effective amount of the compound of formula I is administered to a mammal to be treated in an amount expressed as milligrams per $m^2$ of body surface of said mammal, per day: "$mg/m^2/day$". The dose, i.e., the therapeutically effective amount of a compound of formula I will usually range from about 0.2 $mg/m^2/day$ to about 2000 $mg/m^2/day$, preferably from about 0.5 $mg/m^2/day$ to about 1500 $mg/m^2/day$, more preferably from about 1.0 $mg/m^2/day$ to about 1000 $mg/m^2/day$. In case of a combination of a compound of formula I with a chemotherapeutic agent such as an anticancer agent, administration may be simultaneously, for example given as coformulation or separately, or sequentially. The dose of a compound of formula I will usually be as given above whereas the dose of the chemotherapeutic agent will range from about 0.2 $mg/m^2/day$ to about 2000 $mg/m^2/day$, preferably from about 0.5 $mg/m^2/day$ to about 1500 $mg/m^2/day$, more preferably from about 1.0 $mg/m^2/day$ to about 1000 $mg/m^2/day$.

It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy.

The following examples illustrate the invention without limiting it.

EXAMPLES

General Procedures for the preparation of 3-(indolyl)- and a 3-(azaindolyl)-4-phenylmaleimide derivatives Infrared spectra were recorded on a Thermo Nicolet Avatar 330 FT-IR spectrometer. 1H (300 MHz, digital resolution 0, 3768 Hz) and 13C (75 MHz, digital resolution 1, 1299 Hz) NMR spectra were recorded on a Bruker AC 300. The data are reported as follows: chemical shift in ppm from $Me_4Si$ as external standard, multiplicity and coupling constant (Hz). EI-Mass spectra were recorded on a Varian MAT 44S (80 eV) and FD-Mass spectra on a Finnigan MAT 7 (5 kV). For clarity only the highest measured signal is given for FD-Mass spectra. Melting points/decomposition temperatures were determined on a Büchi apparatus according to Dr. Tottoli and are uncorrected. Where appropriate, column chromatography was performed with Merck silica gel 60 (0.063-0.200 mm). The progress of the reactions was monitored by thin layer chromatography (TLC) performed with Merck silica gel 60 F-254 plates. Where necessary, reactions were carried out in a nitrogen atmosphere using 4 Å molecular sieves. All reagents and solvents were obtained from commercial sources and used as received.

General procedure 1 for the preparation of 3-phenyl-4-indolyl-maleinimides

A modified procedure of Peifer et al. (WO 2006/061212 and J. Med. Chem. 2006, 49(4): 1271-1281) was used to prepare 3-phenyl-4-indolyl-maleinimides.

General procedure 2 for the esterification of N-1 substituted 3-phenyl-4-indolyl-maleinimides Method A:
N-1 substituted 3-phenyl-4-indolyl-maleinimide in dry DMF was slowly added via syringe to a stirred solution of 1-ethyl-3-(3-dimethylaminopropyl)carbodiimide (EDCI), 3 equiv., and N-hydroxybenzotriazole (HOBt), 1 equiv., in dry dimethylformamide (DMF) at 0° C. The reaction mixture was stirred for 24 hours at ambient temperature. After quenching with water and extracting with ethyl acetate, the combined organic layers were dried over MgSO$_4$, filtered and concentrated in vacuo. The oily residue was crystallized from PE/EE: 7/1 at 0° C.
Method B:
4-Dimethylaminopyridine (4-DMAP), 1 equiv., was used instead of HOBt.

General procedure 3 for the preparation of N-1 substituted indole-3-ethylglyoxylate A modified procedure of Faul et al. (J. Org. Chem. 1998, 63(6): 1961-1973) and Zhang et al. (Bioorg. Med. Chem. Lett., 2004, 14(12): 3245-3250) was used. A stirred suspension of indole-3-ethylglyoxylate (1 equiv.), CsCO$_3$ or K$_2$CO$_3$ (1.3 equiv.) and the corresponding aliphatic bromo or chloro substituent in dry DMF was heated to 75-80° C. under nitrogen for 8 hours. The reaction was cooled to RT, diluted with ethyl acetate (40 ml) and filtered. The mixture was washed with water, dried over MgSO$_4$, filtered, concentrated and purified by column chromatography.

Example A

2-Amino-N-(3-(3-(2,5-dioxo-4-(3,4,5-trimethoxyphenyl)-2,5-dihydro-1H-pyrrol-3-yl)-1H-indol-1-yl)propyl)-4-methylpentanamide Tert.-butyl-3-bromopropylcarbamate A modified procedure of Wescott et al. (J. Org. Chem. 2003, 68(26): 10058-10066) was used to prepare the title compound. A solution of NaHCO$_3$ (24.4 mmole; 2.0 g) in 80 ml water, di-tert.-butyldicarbonate (24.4 mmole; 5.33 g) and KBr (48.8 mmole; 5.8 g) were added to a stirred suspension of 3-bromopropylammoniumbromide (24.4 mmole; 5.0 g) in 100 ml chloroform. The reaction was refluxed for 5 hours. After cooling to ambient temperature, the organic layer was separated, the aqueous layer extracted with chloroform and the combined organic layers dried with MgSO$_4$, filtered, concentrated and purified by column chromatography. The title compound was obtained as a colorless oil (19.46 mmole; 80%). $^1$H NMR (300 MHz, CDCl$_3$) 4.73 (bs, 1H; NH); 3.41 (t; $^3$J=6.5 Hz; 2H; CH$_2$Br); 3.24 (m; 2H; CH$_2$N); 2.02 (quint; $^3$J=6.5 Hz; 2H; CH$_2$CH$_2$CH$_2$); 1.41 (s; 9H; C(CH$_3$)$_3$).

Ethyl-2-(1-{3-[(tert.-butoxycarbonyl)amino]propyl}-1H-indol-3-yl)-2-oxoacetate

The general procedure 3 was followed using the above product (7.14 mmole; 1.7 g), ethyl-2-(1H-indol-3-yl)-2-oxoacetate (4.6 mmole; 1.0 g) and CsCO$_3$ (9.21 mmole; 3.0 g). The purification was achieved by column chromatography (petroleum ether/diethylether (PE/EE): 1:1) to yield the title compound as pale yellow crystals (5.3 mmole; 74%). Mp 89-90° C. IR ṽ [cm$^{-1}$]=3392; 2977; 2936; 1727; 1698; 1619; 1515. $^1$H NMR (300 MHz, CDCl$_3$) 8.45 (m; 2H; indole-H); 7.35 (m; 3H; indole-H); 4.63 (bs; 1H; NH); 4.41 (q; $^3$J=7.1 Hz; 2H; OCH$_2$CH$_3$); 4.24 (t; $^3$J=7.1 Hz; 2H; indole-CH$_2$); 3.18 (q; $^3$J=6.1 Hz; 2H; CH$_2$N); 2.09 (m; 2H; CH$_2$CH$_2$CH$_2$); 1.44 (s; 9H; C(CH$_3$)$_3$); 1.43 (t; $^3$J=7.1 Hz; 3H; OCH$_2$CH$_3$).

3-(1-{3-[(Tert.-butoxycarbonyl)amino]propyl}-1H-indol-3-yl)-4-(3,4,5-trimethoxyphenyl)-maleinimide The general procedure 1 was followed, using the above product (6.8 mmole; 2.5 g), 3,4,5-trimethoxyphenylacetamide (6.8 mmole; 1.5 g) and tert.-BuOK (14.4 mmole). The purification was achieved by column chromatography (PE/EE: 1:1) to yield the title compound as orange crystals (2.85 mmole; 42%). Mp 178-179° C. IR ṽ [cm$^{-1}$]=3408 ν(NH); 1714 ν(C=O); 1689 ν(C=O); 1613; 1515. $^1$H NMR (300 MHz, CDCl$_3$) 7.95 (s; 1H; indole-H); 7.60 (bs; 1H; imide-NH); 7.32 (d; $^3$J=8.2 Hz; 1H; indole-H); 7.16 (t; $^3$J=7.2 Hz; 1H; indole-H); 6.85 (t; $^3$J=7.2 Hz; 1H; indole-H); 6.79 (s; 2H; 2×Ar—H); 6.47 (d; $^3$J=8.2 Hz; 1H; indole-H); 4.65 (bs; 1H; NH); 4.26 (t; $^3$J=7.10 Hz; 2H; indole-CH$_2$); 3.85 (s; 3H; OCH$_3$); 3.49 (s; 6H; 2×OCH$_3$); 3.16 (m; 2H; CH$_2$N); 2.11 (m; 2H; CH$_2$CH$_2$CH$_2$); 1.44 (s; 9H; C(CH$_3$)$_3$).

3-(1-[3-Ammoniopropyl]-1H-indol-3-yl)-4-(3,4,5-trimethoxyphenyl)-maleinimide-chloride A stirred solution of the above product (2.5 mmole; 1.32 g) in 150 ml ethanol and 2.3 M ethanolic HCl (11.25 mmole; 4.9 ml) was heated to 80° C. for 3 hours. The precipitate was filtered and washed with ethanol to yield the title compound as orange crystals (2.2 mmole; 88%). Mp 274-275° C. IR ṽ [cm$^{-1}$]=3145 ν(NH); 2958 ν(aliphat. CH); 1761ν(C=O); 1708 ν(C=O); 1597; 1499. $^1$H NMR (300 MHz, CDCl$_3$) 11.11 (s; 1H; imide-NH); 8.07 (s; 1H; indole-H); 7.96 (bs; 3H; NH$_3$); 7.62 (d; $^3$J=8.1 Hz; 1H; indole-H); 7.16 (t; $^3$J=7.7 Hz; 1H; indole-H); 6.80 (t; $^3$J=7.7 Hz; 1H; indole-H); 6.72 (s; 2H; 2×Ar—H); 6.36 (d; $^3$J=8.1 Hz; 1H; indole-H); 4.42 (t; $^3$J=6.7 Hz; 2H; indole-CH$_2$); 3.65 (s; 3H; OCH$_3$); 3.36 (s; 6H; 2×OCH$_3$); 2.75 (dd; 2H; $^3$J=6.7 Hz; $^3$J=12.3 Hz; CH$_2$N); 2.07 (m; 2H; CH$_2$CH$_2$CH$_2$).

Tert.-butyl 1-(3-(3-(2,5-dioxo-4-(3,4,5-trimethoxyphenyl)-2,5-dihydro-1H-pyrrol-3-yl)-1H-indol-1-yl)propylamino)-4-methyl-1-oxopentan-2-ylcarbamate

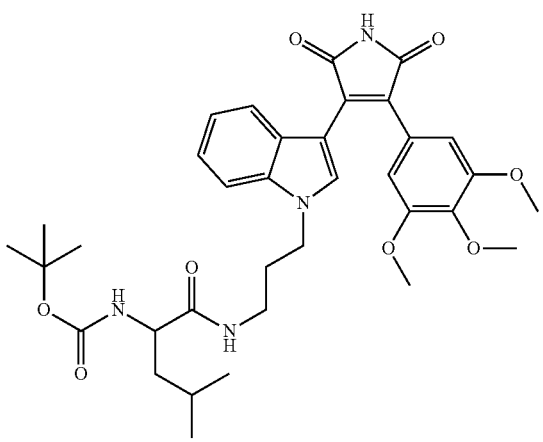

The general procedure 2 (Method A) was followed, using 3-(1-[3-ammoniopropyl]-1H-indol-3-yl)-4-(3,4,5-trimethoxyphenyl)-maleinimide-chloride (0.23 mmol, 0.1 g), 1-ethyl-3-(3-dimethylaminopropyl) carbodiimide (EDCI) (0.66 mmol, 0.125 g), HOBt (0.23 mmol, 0.031 g) and Boc-L-Leu-OH (0.26 mmol). The purification was achieved by crystallization from PE/EE:7/1 to give the title compound as yellow crystals (0.23 mmol; 100%). $R_f$=0.75 (EE). Mp 140-142° C. 1H-NMR (300 MHz, CDCl$_3$) δ[ppm]=7.96 (s, 1H, indole); 7.33 (d, 1H, indole); 7.16 (t, 1H, indole); 6.85 (t, 1H, indole); 6.78 (s, 2H, aryl); 6.46 (d, 1H, indole); 4.81 (m, 1H, NH—CH—CO); 4.26 (t, 2H, indole-CH$_2$); 3.85 (s, 3H, OCH$_3$); 3.48 (s, 6H, OCH$_3$); 3.26 (m, 2H, NH—CH$_2$); 2.14 (m, 2H, —CH$_2$CH$_2$CH$_2$—); 1.64 (m, 2H, CO—CH—CH$_2$); 1.43 (s, 9H, tert.-butyl); 1.25 (m, 1H, CH(CH$_3$)$_2$); 0.92 (d, 6H, CH(CH$_3$)$_2$).

2-Amino-N-(3-(3-(2,5-dioxo-4-(3,4,5-trimethoxyphenyl)-2,5-dihydro-1H-pyrrol-3-yl)-1H-indol-1-yl)propyl)-4-methylpentanamide (Compound A)

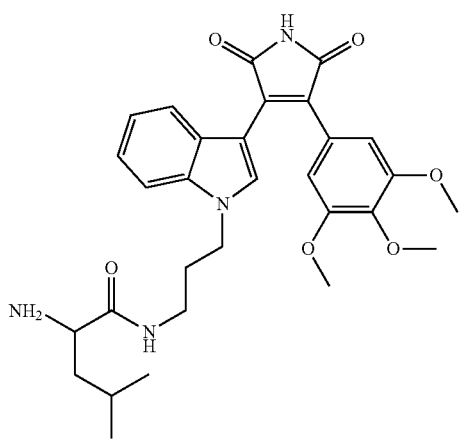

To the above product (0.07 mmol) in dichloromethane (DCM) was added trichloroacetic acid (1.22 mmol) and the mixture was stirred under inert gas at ambient temperature for 24 h. The solution was then concentrated in vacuo, the oily residue diluted with ethyl acetate and washed three times with saturated NaHCO$_3$ solution. The dried organic phase (MgSO$_4$) was concentrated in vacuo and crystallized with petrol ether to give the title compound as orange-red crystals (0.058 mmol, 84%). $R_f$=0.12 (EE). Mp 172-173° C. FD-MS m/z (rel. int.)=548.21 (100%) 1H-NMR (300 MHz, CDCl$_3$) δ[ppm]=7.96 (s, 1H, indole); 7.31 (d, 1H, indole); 7.16 (t, 1H, indole); 6.87 (t, 1H, indole); 6.78 (s, 2H, aryl); 6.46 (d, 1H, indole); 4.26 (t, 2H, indole-CH$_2$); 3.85 (s, 3H, OCH$_3$); 3.63 (t, 1H, CO—CH—NH); 3.49 (s, 6H, OCH$_3$); 3.29 (m, 2H, NH—CH$_2$); 2.14 (m, 2H, —CH$_2$CH$_2$CH$_2$—); 1.70 (m, 2H, CO—CH—CH$_2$); 1.25 (m, 1H, CH(CH$_3$)$_2$); 0.92 (d, 6H, CH(CH$_3$)$_2$).

Example B

2-Amino-N-(3-(3-(2,5-dioxo-4-(3,4,5-trimethoxyphenyl)-2,5-dihydro-1H-pyrrol-3-yl)-1H-indol-1-yl)propyl)-3-hydroxypropanamide Tert.-butyl-3-(benzyloxy)-1-(3-(3-(2,5-dioxo-4-(3,4,5-trimethoxyphenyl)-2,5-dihydro-1H-pyrrol-3-yl)-1H-indol-1-yl)propylamino)-1-oxopropan-2-ylcarbamate

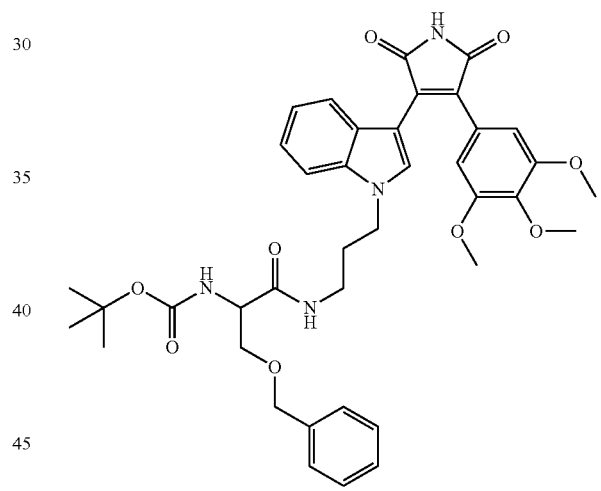

The general procedure 2 was followed, using 3-(1-[3-ammoniopropyl]-1H-indol-3-yl)-4-(3,4,5-trimethoxyphenyl)-maleinimide-chloride (0.34 mmol), EDCI (0.85 mmol), HOBt (0.34 mmol) and Boc-L-serine-O-Bzl-OH (0.34 mmol). The purification was achieved by crystallization from ethyl acetate to give the title compound as yellow-red crystals (0.24 mmol; 71%). Mp 152-154° C. $R_f$=0.70 (EE) 1H-NMR (300 MHz, CDCl$_3$) δ[ppm]=7.89 (s, 1H, indole); 7.33 (d, 1H, indole); 7.32 (m, 5H, Bzl); 7.14 (t, 1H, indole); 6.85 (t, 1H, indole); 6.77 (s, 2H, aryl); 6.53 (d, 1H, indole); 5.41 (m, 1H, CO—CH—NH); 4.53 (m, 1H, Bzl-CH$_a$); 4.28 (m, 1H, Bzl-CH$_{2b}$); 4.18 (t, 2H, indole-CH$_2$); 3.93 (d, 1H, CO—CH—CH$_{2a}$); 3.85 (s, 3H, OCH$_3$); 3.59 (d, 1H, CO—CH—CH$_{2b}$); 3.48 (s, 6H, OCH$_3$); 3.23 (m, 2H, NH—CH$_2$); 2.10 (m, 2H, —CH$_2$CH$_2$CH$_2$—); 1.44 (s, 9H, tert.-butyl).

Tert.-butyl 1-(3-(3-(2,5-dioxo-4-(3,4,5-trimethoxyphenyl)-2,5-dihydro-1H-pyrrol-3-yl)-1H-indol-1-yl)propylamino)-3-hydroxy-1-oxopropan-2-ylcarbamate

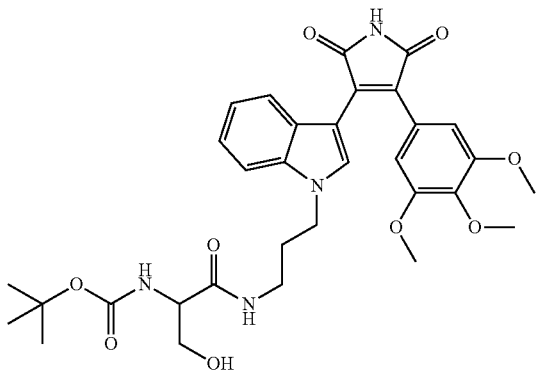 [SMILES: COc1cc(C2=C(c3cn(CCCNC(=O)C(CO)NC(=O)OC(C)(C)C)c4ccccc34)C(=O)NC2=O)cc(OC)c1OC]

To a solution of the above product (0.21 mmol) in abs. DCM was added 10% Pd/C (0.4 equiv.) and the solution was stirred at room temperature for 68 h over $H_2$. The solution was then filtered and concentrated in vacuo to give the title compound as orange-red crystals (0.21 mmol, 100%) which was used directly in the next step. $R_f$=0.43 (EE); Mp 112-114° C.

2-Amino-N-(3-(3-(2,5-dioxo-4-(3,4,5-trimethoxyphenyl)-2,5-dihydro-1H-pyrrol-3-yl)-1H-indol-1-yl)propyl)-3-hydroxypropanamide (Compound B)

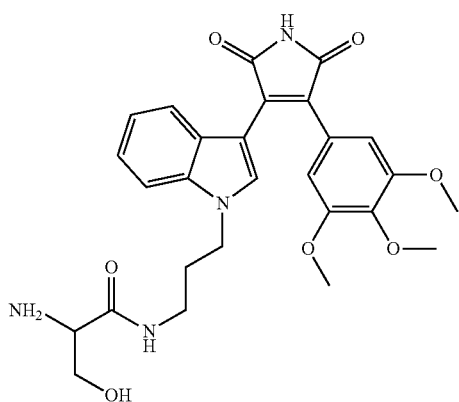 [SMILES: COc1cc(C2=C(c3cn(CCCNC(=O)C(N)CO)c4ccccc34)C(=O)NC2=O)cc(OC)c1OC]

Ethanolic HCl was added to a solution of the above product (0.21 mmol) in ethanol. The mixture was refluxed for 3.5 h, concentrated in vacuo and diluted with a small amount of ethyl acetate. The suspension was filtered to get the title compound as red crystals (0.15 mmol, 72%). Mp 112-114° C. FD-MS m/z (rel. int.)=522.09 (100%). 1H-NMR (300 MHz, CDCl$_3$) δ[ppm]=8.01 (s, 1H, indole); 7.37 (d, 1H, indole); 7.16 (t, 1H, indole); 6.87 (t, 1H, indole); 6.79 (s, 2H, aryl); 6.48 (d, 1H, indole); 4.50 (t, 1H, CO—CH—NH); 4.18 (t, 2H, indole-CH$_2$); 3.94 (d, 1H, CO—CH—C$\underline{H}_{2a}$); 3.59 (d, 1H, CO—CH—C$\underline{H}_{2b}$); 3.85 (s, 3H, OCH$_3$); 3.48 (s, 6H, OCH$_3$); 3.25 (m, 2H, NH—C$\underline{H}_2$); 2.16 (s, 2H, Bzl-C$\underline{H}_2$); 2.09 (m, 2H, —CH$_2$C$\underline{H}_2$CH$_2$—); 1.44 (s, 9H, tert.-butyl).

Example C 3-(3-(2,5-Dioxo-4-(3,4,5-trimethoxyphenyl)-2,5-dihydro-1H-pyrrol-3-yl)-1H-indol-1-yl)propyl 2-amino-4-methylpentanoate 3-Bromopropoxy-tert.-butyldimethylsilane A modified procedure of Galka et al. (J. Lab. Comp. Rad. 2005, 48(11): 797-809) was used to prepare the title compound. A mixture of 3-bromopropanol (39.1 mmole; 5.43 g), tert.-butyldimethylsilylchloride (43.2 mmole; 6.47 g) and imidazole (46.7 mmole; 3.20 g) was stirred at RT for 3 hours under inert gas. The reaction was quenched with water, extracted with diethylether, the organic layer dried over MgSO$_4$, filtered and concentrated. The purification was achieved by column chromatography (PE) to yield the title compound (36.4 mmole; 93%). $^1$H NMR (300 MHz, CDCl$_3$) 3.73 (t; $^3$J=5.7 Hz; 2H; CH$_2$O); 3.51 (t; $^3$J=6.4 Hz; 2H; CH$_2$Br); 2.02 (q; $^3$J=5.7 Hz; $^3$J=6.4 Hz; 2H; CH$_2$C$\underline{H}_2$CH$_2$); 0.89 (s; 9H; C(CH$_3$)$_3$); 0.06 (s; 6H; 2×CH$_3$).

Ethyl-2-(1-{3-[{1-(tert.-butyl)-1,1-dimethylsilyl}oxy]propyl}-1H-indol-3-yl)-2-oxoacetate The general procedure 3 was used to prepare the title compound using the above product (7.9 mmole; 2 g), ethyl-2-(1H-indol-3-yl)-2-oxoacetate (7.4 mmole; 1.61 g) and CsCO$_3$ (10 mmole; 3.25 g). The purification was achieved by column chromatography (PE/EE: 9:1) to yield the title compound as pale yellow crystals (6.7 mmole; 91%). Mp 51-52° C. $^1$H NMR (300 MHz, CDCl$_3$) 8.46 (m; 1H; indole-H); 8.37 (s; 1H; indole-H); 7.43 (m; 1H; indole-H); 7.34 (m; 2H; indole-H); 4.41 (q; $^3$J=7.1 Hz; 2H; OC$\underline{H}_2$CH$_3$); 4.33 (t; $^3$J=6.8 Hz; 2H; indole-CH$_2$); 3.58 (t; $^3$J=5.5 Hz; 2H; CH$_2$O); 2.06 (m; 2H; indole-CH$_2$C$\underline{H}_2$CH$_2$O); 1.43 (t; J=7.1 Hz; 3H OCH$_2$C$\underline{H}_3$); 0.94 (s; 9H); 0.07 (s; 6H).

3-(1-{3-[{1-(Tert.-butyl)-1,1-dimethylsilyl}oxy] propyl}-1H-indol-3-yl)-4-(3,4,5-trimethoxyphenyl)-maleinimide The general procedure 1 was then followed, using the above product (6.7 mmole; 2.64 g), 3,4,5-trimethoxyphenylacetamide (6.04 mmole; 1.36 g) and tert.-BuOK (18 mmole). The purification was achieved by column chromatography (PE/EE: 7/3) to yield the title compound as yellow crystals (3 mmole; 45%). Mp 99-100° C. $^1$H NMR (300 MHz, CDCl$_3$) 8.30 (bs; 1H; imide-NH); 7.98 (s; 1H; indole-H); 7.38 (d; $^3$J=8.1 Hz; 1H; indole-H); 7.15 (t; $^3$J=7.6 Hz; 1H; indole-H); 6.85 (t; $^3$J=7.6 Hz; 1H; indole-H); 6.80 (s; 2H; Ar—H); 6.47 (d; $^3$J=8.1 Hz; 1H; indole-H); 4.34 (t; $^3$J=6.8 Hz; 2H; indole-C$\underline{H}_2$CH$_2$CH$_2$O); 3.86 (s; 3H; OCH$_3$); 3.60 (t; $^3$J=5.5 Hz; 2H indole-CH$_2$CH$_2$CH$_2$O); 3.49 (s; 6H; 2×OCH$_3$); 2.08 (m; 2H; indole-CH$_2$CH$_2$CH$_2$O); 0.94 (s; 9H; SiC(CH$_3$)$_3$); 0.07 (s; 6H; Si(CH$_3$)$_2$).

3-(1-[3-Hydroxypropyl]-1H-indol-3-yl)-4-(3,4,5-trimethoxyphenyl)-maleinimide A modified procedure of Csuk et al. (Z. Naturforsch., 2003, 58b: 97-105) was used to prepare the title compound. Tetrabutylammoniumfluoride (3.5 mmole; 1.08 g) was added to a stirred solution of the above product (3 mmole; 1.65 g) in 20 ml tetrahydrofurane (THF). After the reaction was completed it was concentrated. The purification was achieved by column chromatography (PE/EE: 1:8) to yield the title compound as orange crystals (2.25 mmole; 75%). Mp 160-161° C. $^1$H NMR (300 MHz, CDCl$_3$) 7.97 (s; 1H; indole-NH); 7.38 (m; 2H; indole-H+imide-NH); 7.17 (t; $^3$J=7.6 Hz; 1H; indole-H); 6.86 (t; $^3$J=7.6 Hz; 1H; indole-H); 6.79 (s; 2H; Ar—H); 6.49 (d; $^3$J=8.1 Hz; 1H; indole-H); 4.39 (t; $^3$J=6.79 Hz; 2H; indole-CH$_2$CH$_2$CH$_2$O); 3.86 (s; 3H; OCH$_3$); 3.65 (t; $^3$J=5.67 Hz; 2H; indole-CH$_2$CH$_2$CH$_2$O); 3.50 (s; 6H; 2×OCH$_3$); 2.13 (m, 2H; indole-CH$_2$CH$_2$CH$_2$O).

3-(3-(2,5-Dioxo-4-(3,4,5-trimethoxyphenyl)-2,5-dihydro-1H-pyrrol-3-yl)-1H-indol-1-yl)propyl 2-(tert.-butoxycarbonylamino)-4-methylpentanoate

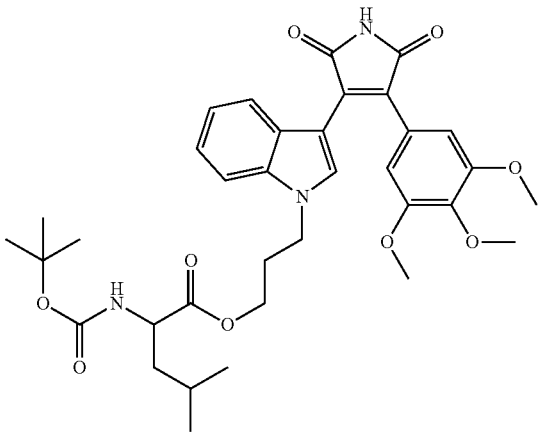 [SMILES: COc1cc(C2=C(c3cn(CCCOC(=O)C(CC(C)C)NC(=O)OC(C)(C)C)c4ccccc34)C(=O)NC2=O)cc(OC)c1OC]

The general procedure 2 (Method B) was followed, using 3-(1-[3-hydroxypropyl]-1H-indol-3-yl)-4-(3,4,5-trimethoxyphenyl)-maleinimide (0.46 mmol), EDCI (0.65 mmol), 4-DMAP (0.09 mmol) and Boc-L-Leu-OH (0.46 mmol). The purification was achieved by crystallization from petrol ether to give the title compound as red crystals (0.46 mmol; 100%). FD-MS m/z (rel. int.)=549.26 (100%). $^1$H-NMR (300 MHz, CDCl$_3$) δ[ppm]=7.96 (s, 1H, indole); 7.33 (d, 1H, indole); 7.16 (t, 1H, indole); 6.85 (t, 1H, indole); 6.78 (s, 2H, aryl); 6.45 (d, 1H, indole); 4.89 (m, 1H, NHCHCO) 4.32 (t, 2H, indole-CH$_2$); 4.10 (m, 2H, —O—CH$_2$); 3.85 (s, 3H, OCH$_3$); 3.48 (s, 6H, OCH$_3$); 2.26 (m, 2H, CH$_2$—CH$_2$—CH$_2$); 1.67 (m, 2H, CO—CH—CH$_2$); 1.43 (s, 9H, tert.-butyl); 1.25 (m, 1H, CH(CH$_3$)$_2$); 0.92 (d, 6H, CH(CH$_3$)$_2$).

3-(3-(2,5-Dioxo-4-(3,4,5-trimethoxyphenyl)-2,5-dihydro-1H-pyrrol-3-yl)-1H-indol-1-yl)propyl 2-amino-4-methylpentanoate (Compound C)

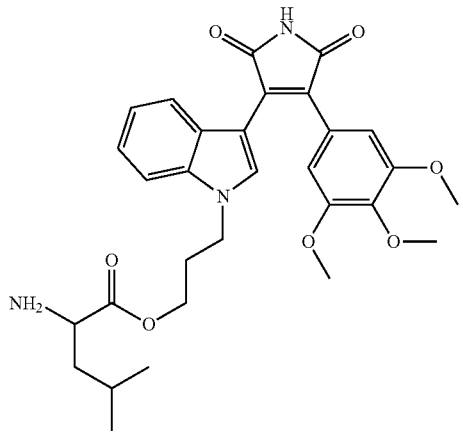 [SMILES: COc1cc(C2=C(c3cn(CCCOC(=O)C(N)CC(C)C)c4ccccc34)C(=O)NC2=O)cc(OC)c1OC]

Ethanolic HCl was added to a solution of the above product (0.46 mmol) in ethanol. The mixture was refluxed for 3.5 h, concentrated in vacuo and diluted with a small amount of ethyl acetate. The suspension was filtered to get the title compound as red crystals (0.32 mmol, 69%). 1H-NMR (300 MHz, CDCl$_3$) δ[ppm]=7.96 (s, 1H, indole); 7.33 (d, 1H, indole); 7.16 (t, 1H, indole); 6.85 (t, 1H, indole); 6.78 (s, 2H, aryl); 6.45 (d, 1H, indole); 4.67 (m, 1H, NHCHCO) 4.32 (t, 2H, indole-CH$_2$); 4.10 (m, 2H, —O—CH$_2$); 3.85 (s, 3H, OCH$_3$); 3.48 (s, 6H, OCH$_3$); 2.26 (m, 2H, CH$_2$—CH$_2$—CH$_2$); 1.67 (m, 2H, CO—CH—CH$_2$); 1.25 (m, 1H, CH(CH$_3$)$_2$); 0.92 (d, 6H, CH(CH$_3$)$_2$).

Example D

2-(3-(2,5-Dioxo-4-(3,4,5-trimethoxyphenyl)-2,5-dihydro-1H-pyrrol-3-yl)-1H-indol-1-yl)ethyl 2-amino-4-methylpentanoate

2-Bromoethoxy-tert.-butyl-dimethylsilane

The title compound was synthesized using the same procedure as for example C to yield 6.4 mmole; 96%. $^1$H NMR (300 MHz, CDCl$_3$) 3.91 (t; $^3$J=6.5 Hz; 2H; OCH$_2$); 3.41 (t; $^3$J=6.5 Hz; 2H; CH$_2$Br); 0.93 (s; 9H; C(CH$_3$)$_3$); 0.11 (s; 6H; 2×CH$_3$).

Ethyl-2-(1-{2-[{1-(tert.-butyl)-1,1-dimethylsilyl}oxy]ethyl}-1H-indol-3-yl)-2-oxoacetate The general procedure 3 was then followed, using the above product (6.4 mmole; 1.53 g), ethyl-2-(1H-indol-3-yl)-2-oxoacetate (5.99 mmole; 1.3 g) and CsCO$_3$ (8.1 mmole; 2.63 g). The purification was achieved by column chromatography (PE/EE: 7/3) to yield the title compound as pale yellow oil (4.37 mmole; 73%). $^1$H NMR (300 MHz, CDCl$_3$) 8.45 (m; 1H; indole-H); 8.42 (s; 1H; indole-H); 7.37 (m; 3H; indole-H); 4.41 (q; $^3$J=7.1 Hz; 2H; OCH$_2$CH$_3$); 4.29 (t; $^3$J=5.1 Hz; 2H; indole-CH$_2$CH$_2$O); 3.95 (t; $^3$J=5.1 Hz; 2H indole-CH$_2$CH$_2$O); 1.43 (t; $^3$J=7.1 Hz; 3H; OCH$_2$CH$_3$); 0.80 (s; 9H; C(CH$_3$)$_3$); −0.17 (s; 6H; 2×CH$_3$).

3-(1-{2-[{1-(Tert.-butyl)-1,1-dimethylsilyl}oxy]ethyl}-1H-indol-3-yl)-4-(3,4,5-trimethoxyphenyl)-maleinimide The general procedure 1 was then followed, using the above product (1.8 mmole; 0.69 g), 3,4,5-trimethoxyphenylacetamide (1.6 mmole; 0.36 g) and tert.-BuOK (6 mmole). The purification was achieved by column chromatography (PE/EE: 7/3) to yield the title compound as yellow crystals (0.8 mmole; 44%). $^1$H NMR (300 MHz, CDCl$_3$) 8.06 (s; 1H; indole-H); 7.34 (d; $^3$J=8.1 Hz; 2H; indole-H); 7.29 (bs, 1H; imide-NH) 7.15 (t; $^3$J=7.5 Hz; 1H; indole-H); 6.84 (t; $^3$J=7.5 Hz; 1H; indole-H); 6.77 (s; 2H; Ar—H); 6.42 (d; $^3$J=8.1 Hz; 1H; indole-H); 4.31 (t; $^3$J=5.2 Hz; 2H; indole-C$\underline{H}_2$CH$_2$O); 3.98 (t; $^3$J=5.2 Hz; 2H indole-CH$_2$C$\underline{H}_2$O); 3.86 (s; 3H; OCH$_3$); 3.50 (s; 6H; 2×OCH$_3$); 0.82 (s; 9H; C(CH$_3$)$_3$); −0.13 (s; 6H; Si(CH$_3$)$_2$).

3-(1-[2-Hydroxyethyl]-1H-indol-3-yl)-4-(3,4,5-trimethoxyphenyl)-maleinimide

The same procedure as for example C was used to prepare the title compound as dark red crystals (0.4 mmole; 58%). Mp 195-196° C. $^1$H NMR (300 MHz, CDCl$_3$) 8.02 (s; 1H; indole-H); 7.37 (d; $^3$J=7.9 Hz; 1H; indole-H); 7.32 (s; 1H; imide-NH); 7.17 (t; $^3$J=7.7 Hz; 1H; indole-H); 6.87 (t; $^3$J=7.7 Hz; 1H; indole-H); 6.79 (s; 2H; Ar—H); 6.50 (d; $^3$J=7.9 Hz; 1H; indole-H); 4.37 (t; $^3$J=5.2 Hz; 2H; indole-CH$_2$); 4.06 (q; $^3$J=5.0 Hz; 2H; CH$_2$O); 3.86 (s; 3H; OCH$_3$); 3.50 (s; 6H; 2×OCH$_3$).

2-(3-(2,5-Dioxo-4-(3,4,5-trimethoxyphenyl)-2,5-dihydro-1H-pyrrol-3-yl)-1H-indol-1-yl)ethyl 2-(tert.-butoxycarbonylamino)-4-methylpentanoate

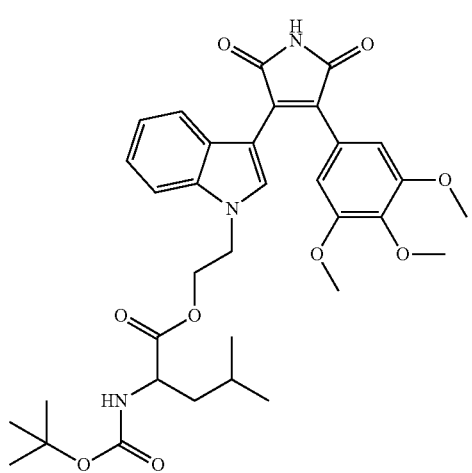 [SMILES: COc1cc(C2=C(c3cn(CCOC(=O)C(CC(C)C)NC(=O)OC(C)(C)C)c4ccccc34)C(=O)NC2=O)cc(OC)c1OC]

The general procedure 2 (Method B) was followed, using 3-(1-[2-hydroxyethyl]-1H-indol-3-yl)-4-(3,4,5-trimethoxyphenyl)-maleinimide (0.47 mmol), EDCI (0.65 mmol), 4-DMAP (0.09 mmol) and Boc-L-Leu-OH (0.47 mmol). The purification was achieved by crystallization from petrol ether to give the title compound as orange crystals (0.40 mmol; 85%). 1H-NMR (300 MHz, CDCl$_3$) δ[ppm]=7.98 (s, 1H, indole); 7.33 (d, 1H, indole); 7.18 (t, 1H, indole); 6.87 (t, 1H, indole); 6.78 (s, 2H, aryl); 6.46 (d, 1H, indole); 4.99 (m, 1H, NH—C$\underline{H}$—CO); 4.47 (m, 2H, indole-CH$_2$); 4.46 (m, 1H, O—C$\underline{H}_{2a}$); 4.24 (m, 1H, O—C$\underline{H}_{2b}$); 3.85 (s, 3H, OCH$_3$); 3.49 (s, 6H, OCH$_3$); 1.62 (m, 2H, CO—CH—C$\underline{H}_2$); 1.40 (s, 9H, tert.-butyl); 1.24 (m, 1H, C$\underline{H}$(CH$_3$)$_2$); 0.92 (d, 6H, CH(C$\underline{H}_3$)$_2$).

2-(3-(2,5-Dioxo-4-(3,4,5-trimethoxyphenyl)-2,5-dihydro-1H-pyrrol-3-yl)-1H-indol-1-yl)ethyl 2-amino-4-methylpentanoate (Compound D)

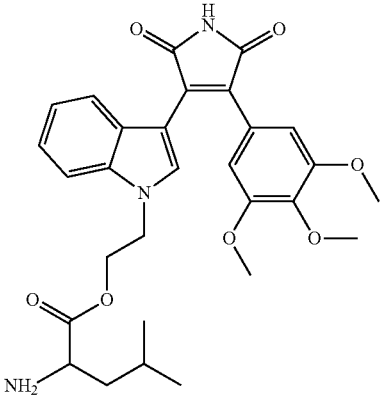 [SMILES: COc1cc(C2=C(c3cn(CCOC(=O)C(N)CC(C)C)c4ccccc34)C(=O)NC2=O)cc(OC)c1OC]

Ethanolic HCl was added to a solution of the above product (0.40 mmol) in ethanol. The mixture was refluxed for 3.5 h, concentrated in vacuo and diluted with a small amount of ethyl acetate. The suspension was filtered to get the title compound as red crystals (0.27 mmol, 68%). FD-MS m/z (rel. int.)=535.23 (100%) 1H-NMR (300 MHz, CDCl$_3$) δ[ppm]=7.97 (s, 1H, indole); 7.33 (d, 1H, indole); 7.18 (t, 1H, indole); 6.87 (t, 1H, indole); 6.78 (s, 2H, aryl); 6.46 (d, 1H, indole); 4.60 (m, 1H, NH—C$\underline{H}$—CO); 4.49 (m, 2H, indole-C$\underline{H}_2$); 4.47 (m, 1H, O—C$\underline{H}_{2a}$); 4.37 (m, 1H, O—C$\underline{H}_{2b}$); 3.85 (s, 3H, OCH$_3$); 3.49 (s, 6H, OCH$_3$); 1.61 (m, 2H, CO—CH—CH2); 1.23 (m, 1H, CH(CH3)2); 0.87 (d, 6H, CH(CH3)2).

Example 1

Biological effects of 3-(indolyl)- and 3-(azaindolyl)-4-phenylmaleimide derivatives of formula I 3-(indolyl)- and 3-(azaindolyl)-4-phenylmaleimide derivatives of the present invention were investigated for their effect on the viability of vascular endothelial, colon cancer cell lines and for their inhibitory effect on different protein kinases.

GSK-3β, VEGFR-2, FLT-3, Kinase Assays

The effect of test compounds on the activity of the protein kinases GSK-3β, VEGFR-2 and FLT-3 was evaluated based on half maximal inhibitory concentration (IC$_{50}$) values determined by Millipore UK Ltd; Gemini Crescent; Dundee Technology Park; Dundee DD2 1SW; UK (IC$_{50}$Profiler). Detailed protocols can be found at: www.millipore.com/drugdiscovery/dd3/assayprotocols.

Evaluation of Antiproliferative Effect (MTT Assay)

The antiproliferative activity of test compounds was determined by the 3-(4,5-dimethylthiazol-2-yl)-2,5-diphenyltetrazolium bromide (MTT) assay as described previously (Mosmann, T. et al. (1983) J. Immunol. Methods 65: 55-63). Cells in the exponential growth phase were transferred to 96-well flat-bottomed plates. 10,000 viable cells contained in 200 µl cell suspension were plated into each well and incubated over night. Cells were then exposed to various concentrations of test compounds (100 μl/well) for 3 days at 37° C. with 5% $CO_2$. Subsequently, 10 μl/well MTT stock solution (5 mg/ml; Biomol, Germany) were added and the cells were incubated at 37° C. with 5% $CO_2$ for 4 hours. 100 μl solubilization solution (10% SDS in 0.01 M HCl) were added and the cells were incubated at 37° C. with 5% $CO_2$ over night. Plates were read on an ELISA-Reader ELX 800 (BIO-TEK Software KC 4) at 562 nm absorbance. Each experiment was done in triplicate.

Nicoletti Apoptosis Assay by Cell Cycle Analysis

Cancer cells were transferred to 12-well flat-bottomed plates. $1.5 \times 10^5$ viable cells contained in 1 ml cell suspension were plated into each well and incubated over night before exposure with various concentrations of drugs. Subsequently, cells were incubated in 1 ml medium containing various concentrations of test compounds at 37° C. with 5% $CO_2$. After incubation the cells were washed with PBS, trypsinized, pelleted and mixed with PI buffer (containing 0.1% sodium citrate, 0.1% triton X-100, 50 mg/ml propidium iodide (PI)) and incubated for 1 hour at 4° C. Cell cycle sub-G1 fraction analysis was performed as described previously (Nicoletti, I. et al. (1991) J. Immunol. Methods 139: 271-279) using a flow cytometer (BD FACS Calibur™, BD Biosciences, Heidelberg, Germany). Each experiment was done in triplicate.

Drugs

Working solutions of 26 mM test compound in DMSO were prepared and stored in aliquots at −20° C. A 29.6 mM stock solution of irinotecan in water was prepared and stored in aliquots at 4° C. The drugs were diluted in culture medium immediately before use to obtain the desired concentrations.

Cell Lines

The human colon cancer cell line HT-29 was obtained from the DSMZ, Germany. JT29 cells were cultured in RPMI 1640 supplemented with 10% FCS at 37° C. and 5% $CO_2$.

Example 1.1

Selectivity Profiles of Compounds of Formula I for Protein Kinases VEGFR-2, FLT-3 and GSK-3β

The inhibitory effect of test compounds on protein kinases VEGFR-2, FLT-3 and GSK-3β was investigated using respective kinase inhibition assays (method described above) and the values of half maximal inhibitory concentration ($IC_{50}$) were determined from the assay results. Structural differences of the compounds of formula I resulted in differentiated biological profiles of these compounds (see Table 1). Thus, compounds with selective kinase profiles were identified, which may allow application specific for a certain tumor or condition while showing less side-effects caused by activity against other kinases.

TABLE 1

Determination of $IC_{50}$ in VEGFR-2, FLT-3 and GSK-3β kinase assays

| Compound | $IC_{50}$ [nM] | | |
|---|---|---|---|
| | VEGFR-2 | FLT-3 | GSK-3β |
| A | ≥1000 | ≥1000 | 208 |
| C | ≥1000 | 480 | 134 |
| D | 251 | 239 | 12 |

Example 1.2

In Vitro Analysis of Antineoplastic Properties of Compounds of Formula I

The antitumor activity of test compounds was examined against HT-29 human colon adenocarcinoma cells using MTT assay (method described above). All tested compounds showed initial dose dependent cytotoxicity when used in concentrations up to low micromolar range (see Table 2).

TABLE 2

Decrease of HT-29 colon cancer cell viability by treatment with test compounds

| Compound | Viability of HT-29 cells [%] as determined by MTT assay | | |
|---|---|---|---|
| Conc. | A | C | D |
| 1 μM | 94.9 ± 4.6 | 96.7 ± 3.3 | 104.3 ± 6.4 |
| 10 μM | 68.7 ± 0.9 | 49.3 ± 1.1 | 99.4 ± 8.3 |
| 20 μM | 59.2 ± 5.4 | 51.0 ± 2.3 | 94.5 ± 8.3 |
| 50 μM | 26.0 ± 8.9 | not determined | 65.3 ± 3.3 |

Example 1.3

In Vitro Analysis of Effects of Combinations of Compounds of Formula I and Toposiomerase I Inhibitors on Apoptosis in Human Colon Cancer Cells Compounds of the invention (test compounds) and the topoisomerase I inhibitor irinotecan were analyzed for their individual and combined effect in apoptosis assay (method described above). Induction of apoptosis was determined by cell cycle analysis (% sub-G1 fraction) after incubating HT-29 cells with test compounds, irinotecan or combinations thereof, respectively, for 7 days. The combination of test compounds and low dosed irinotecan synergistically enhanced apoptosis of HT-29 cells (see Table 3).

TABLE 3

Enhancement of apoptosis in human colon and gastric adenocarcinoma cell lines by combining test compounds and irinotecan

| | Sub-G1 Fraction [%] | | |
|---|---|---|---|
| | A | C | D |
| 8 μM test compound only | 7.4 ± 0.5 | 6.6 ± 0.4 | 6.2 ± 0.8 |
| 8 μM test compound plus 1.18 μM irinotecan | 38.9 ± 2.8 | 39.2 ± 0.7 | 44.5 ± 1.5 |
| 1.18 μM irinotecan only | | 26.1 ± 2.1 | |
| drug-free control | | 9.2 ± 0.6 | |

Example 2

In vitro hepatic microsome stability of 3-(indolyl)- and 3-(azaindolyl)-4-phenylmaleimide derivatives of formula (I)

Metabolic conversion was evaluated by incubating compounds of the invention (test compounds) with rat liver microsomes (BD Biosciences) in Tris buffer.

A time dependent degradation of compound C (molecular weight (MW): 549) and increasing concentration of its metabolite C1 (3-(1-(3-hydroxypropyl)indol-3-yl)-4-(3,4,5- trimethoxyphenyl)-1H-pyrrole-2,5-dione) were observed. Subsequent degradation of C1 gave its metabolite Z1 (3-(1-H-indol-3-yl)-4-(3,4,5-trimethoxyphenyl)-1H-pyrrole-2,5-dione). Z1 was metabolized to form metabolite Z2 (3-(4-hydroxy-3,5-dimethoxy-phenyl)-4-(1-H-indol-3-yl)-1H-pyrrole-2,5-dione).

Compound D was found to yield metabolite D1 (3-(1-(3-hydroxypropyl)indol-3-yl)-4-(3,4,5-trimethoxyphenyl)-1H-pyrrole-2,5-dione) which upon further degradation gave compound Z1 which was further degraded to Z2.

The inhibitory effects of metabolites of compounds C and D on protein kinases VEGFR-2, FLT-3 and GSK-3β are summarized in Table 4.

TABLE 4

$IC_{50}$ of metabolites in VEGFR-2, FLT-3 and GSK-3β kinase assays

| Compound | $IC_{50}$ [nM] | | |
|---|---|---|---|
| | VEGFR-2 | FLT-3 | GSK-3β |
| C1 | 920 | 556 | 2254 |
| D1 | 153 | 554 | 3386 |
| Z1 | 90 | 270 | >1000 |

Embodiments of the Invention

E1. 3-(Indolyl)- and 3-(azaindolyl)-4-phenylmaleimide compounds of formula I

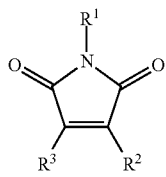
(I)

wherein $R^1$ is —H, $C_1$-$C_6$-alkyl, phenyl-$C_1$-$C_4$-alkyl or phenyl;

$R^2$ is a phenyl group which is substituted with 2 or 3 $C_1$-$C_6$-alkoxy groups; and $R^3$ is selected from:

a)
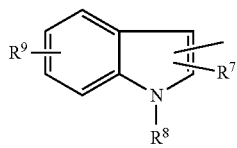

b)
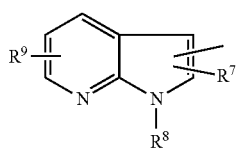

c)
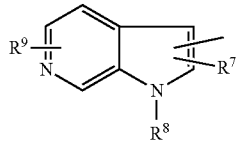

d)
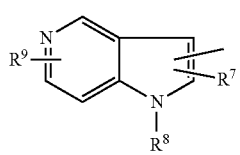

e)
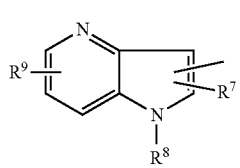

wherein $R^7$ is —H, $C_1$-$C_6$-alkyl or phenyl;

$R^9$ is —H, $C_1$-$C_6$-alkyl, $C_1$-$C_6$-alkoxy, —OH, halogen, —NH$_2$, $C_1$-$C_6$-alkylamino, di-$C_1$-$C_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S; and $R^8$ is —$C_1$-$C_8$-alkyl-$X^1$—$X^2$—$R^{10}$, —$C_2$-$C_8$-alkenyl-$X^1$—$X^2$—$R^{10}$ or —$C_2$-$C_8$-alkynyl-$X^1$—$X^2$—$R^{10}$, and is preferably —$C_1$-$C_8$-alkyl-$X^1$—$X^2$—$R^{10}$, wherein $X^1$ is a single bond, —(OCH$_2$CH$_2$)$_n$—, or —(OCH$_2$CH$_2$CH$_2$)$_n$—, wherein n is 1, 2 or 3;

$X^2$ is —OC(O)—, —NR$^{11}$C(O)—, —C(O)O—, —C(O)NR$^{11}$—, —OC(O)NR$^{11}$—, —NR$^{11}$C(O)O—, —NR$^{12}$C(O)NR$^{12}$—, —OS(O)$_2$—, —S(O)$_2$O—, —OS(O)$_2$O—, —NR$^{11}$—, —O—, —S—, or

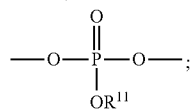

$R^{10}$ is selected from a) linear or branched $C_1$-$C_6$-alkyl substituted with one group selected from —NHR$^{11}$, —OH, —SH, —C(O)OH and —S(O)$_2$OH, and optionally further substituted with one, two or three groups independently selected from —NHR$^{13}$, —OH, —SR$^{13}$, —C(O)OH, —S(O)$_2$OH, —C(O)NH$_2$, —NHC(NH)NH$_2$, —NHC(O)NH$_2$, $C_3$-$C_7$-cycloalkyl, aryl, in particular phenyl, and 5- or 6-membered heteroaryl, in particular indolyl or imidazolyl, said cycloalkyl being optionally being substituted with one or two $C_1$-$C_6$-alkyl, and said aryl and heteroaryl being optionally substituted with one, two, three or four groups independently selected from —OH, $C_1$-$C_6$-alkyl and —C(O)OH;

b) a 5- or 6-membered saturated heterocyclyl, in particular pyrrolidinyl, optionally substituted with one, two or three groups independently selected from $C_1$-$C_6$-alkyl, —OH and —C(O)OH;

c) $C_1$-$C_6$-alkyl substituted with monocyclic or bicyclic heteroaryl, in particular with imidazolyl, such as 5-imidazolyl, said heteroaryl being optionally substituted with one, two, three or four groups independently selected from —OH, $C_1$-$C_6$-alkyl and —C(O)OH;

d) monocyclic or bicyclic aryl, optionally substituted with one, two, three or four groups independently selected from —OH, $C_1$-$C_6$-alkyl, or —C(O)OH;

e) $C_3$-$C_7$-cycloalkyl optionally substituted with one or two $C_1$-$C_6$-alkyl;

f) monocyclic or bicyclic heteroaryl, optionally substituted with one, two, three or four groups independently selected from —OH, $C_1$-$C_6$-alkyl and —C(O)OH;

g) $C_1$-$C_6$-alkyl substituted with monocyclic or bicyclic aryl, in particular with phenyl, said aryl being optionally substituted with one, two or three groups independently selected from —OH, $C_1$-$C_6$-alkyl and —C(O)OH;

h) —(CH$_2$CH$_2$O)$_m$H, —(CH(CH$_3$)CH$_2$O)$_m$H, or —(CH$_2$CH(CH$_3$)O)$_m$H, wherein m is 1 to 10; and $R^{11}$ is selected from —H, $C_1$-$C_6$-alkyl, phenyl and benzyl;

$R^{12}$ is —H or $C_1$-$C_8$-alkyl; and $R^{13}$ is selected from —H, $C_1$-$C_6$-alkyl, phenyl and benzyl;

and the physiologically acceptable salts, solvates and solvates of the salts of the compounds of formula I.

E2. The compounds of E1, wherein $R^2$ is a group having the formula

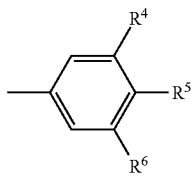

wherein $R^4$, $R^5$ and $R^6$ are $C_1$-$C_6$-alkoxy.

E3. The compounds of E1 or E2
having formula Ia:

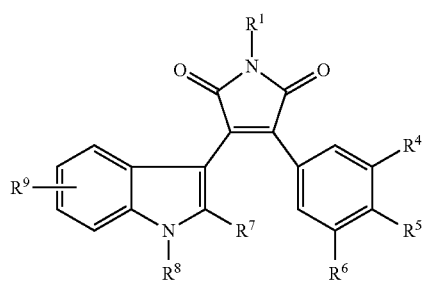
(Ia)

wherein $R^1$, $R^7$, $R^8$ and $R^9$ are as defined in E1 and $R^4$, $R^5$ and $R^6$ are $C_1$-$C_6$-alkoxy.

E4. The compounds of E1 or E2
having formula Ib:

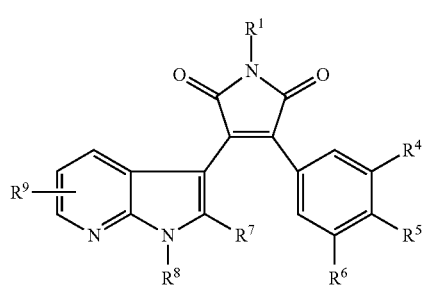
(Ib)

wherein $R^1$, $R^7$, $R^8$ and $R^9$ are as defined in E1 and $R^4$, $R^5$ and $R^6$ are $C_1$-$C_6$-alkoxy.

E5. The compounds of E1 or E2
having formula Ic:

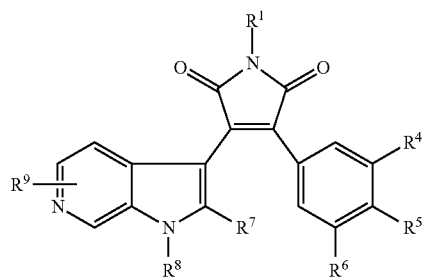
(Ic)

wherein $R^1$, $R^7$, $R^8$ and $R^9$ are as defined in E1 and $R^4$, $R^5$ and $R^6$ are $C_1$-$C_6$-alkoxy.

E6. The compounds of E1 or E2
having formula Id:

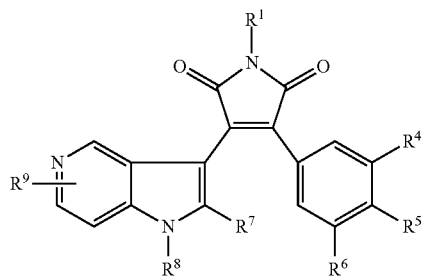
(Id)

wherein $R^1$, $R^7$, $R^8$ and $R^9$ are as defined in E1 and $R^4$, $R^5$ and $R^6$ are $C_1$-$C_6$-alkoxy.

E7. The compounds of E1 or E2
having formula Ie:

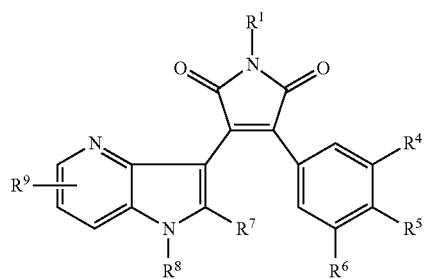
(Ie)

wherein $R^1$, $R^7$, $R^8$ and $R^9$ are as defined in E1 and $R^4$, $R^5$ and $R^6$ are $C_1$-$C_6$-alkoxy.

E8. The compounds of E1 or E2 having a formula as defined in any one of E3 to E7.

E9. The compounds of any one of E1, E2 and E8 having a formula as defined in E5 to E7.

E10. The compounds of any one of E1 to E9, wherein $R^1$ is —H.

E11. The compounds of any one of E1 to E10, wherein $R^7$ is —H.

E12. The compounds of any one of E1 to E11, wherein $R^9$ is —H, $C_1$-$C_6$-alkyl or halogen.

E13. The compounds of any one of E1 to E12, wherein $R^9$ is —H.

E14. The compounds of any one of E1 to E13, wherein $X^1$ is a single bond.

E15. The compounds of any one of E1 to E13, wherein $X^1$ is —(OCH$_2$CH$_2$)$_n$—, or —(OCH$_2$CH$_2$CH$_2$)$_n$—, and n is 1, 2 or 3.

E16. The compounds of any one of E1 to E15, wherein $X^2$ is selected from —OC(O)—, —NR$^{11}$C(O)—, —C(O)O—, —C(O)NR$^{11}$—, —OC(O)NR$^{11}$—, —NR$^{11}$C(O)O—, —NR$^{12}$C(O)NR$^{12}$—, —NR$^{11}$— and —O—.

E17. The compounds of any one of E1 to E14 and E16, wherein $X^1$ is a single bond and $X^2$ is selected from —OC(O)—, —C(O)O—, —NR$^{11}$C(O)—, —C(O)NR$^{11}$— and —NR$^{12}$C(O)NR$^{12}$—.

E18. The compounds of any one of E1 to E17, wherein $R^{19}$ is selected from
a) linear or branched $C_1$-$C_6$-alkyl substituted with one residue selected from —NHR$^{11}$, —OH, —SH and —C(O)OH, and optionally further substituted with one, two or three residues independently selected from —NHR$^{13}$, —OH, —SR$^{13}$, —C(O)OH, —C(O)NH$_2$, —NHC(NH)NH$_2$, —NHC(O)NH$_2$, phenyl, hydroxyphenyl, indolyl and imidazolyl, said indolyl or imidazolyl being optionally substituted with one, two, three or four residues independently selected from —OH, $C_1$-$C_6$-alkyl and —C(O)OH;
b) 5- or 6-membered saturated heterocyclyl, in particular pyrrolidinyl, optionally substituted with one or two residues independently selected from $C_1$-$C_6$-alkyl, —OH and —C(O)OH; and
c) $C_1$-$C_6$-alkyl substituted with imidazolyl.

E19. The compounds of any one of E1 to E14 and E16 to E18, wherein $R^8$ is —$C_1$-$C_8$-alkyl-OC(O)—$R^{10}$ or —$C_1$-$C_8$-alkyl-NR$^{11}$C(O)—$R^{10}$.

E20. The compounds of any one of E1 to E14 and E16 to E18, wherein $R^8$ is —$C_1$-$C_6$-alkyl-C(O)O—$R^{10}$ or —$C_1$-$C_6$-alkyl-NR$^{11}$C(O)O—$R^{10}$.

E21. The compounds of any one of E1 to E20, wherein $R^{10}$ is linear or branched $C_1$-$C_6$-alkyl substituted with one —NHR$^{11}$, and optionally further substituted with one, two or three groups independently selected from —NHR$^{13}$, —OH, —SR$^{13}$, —C(O)OH, —S(O)$_2$OH, —C(O)NH$_2$, —NHN(H)NH$_2$, —NHC(O)NH$_2$, aryl and 5- or 6-membered heteroaryl, said aryl and heteroaryl being optionally substituted with one, two, three or four groups independently selected from —OH, $C_1$-$C_6$-alkyl and —C(O)OH.

E22. The compounds of E21, wherein $R^{10}$ is linear or branched $C_1$-$C_6$-alkyl substituted with one —NHR$^{11}$, and further substituted with one, two or three groups independently selected from —NHR$^{13}$, —OH, —SR$^{13}$, —C(O)OH, —S(O)$_2$OH, —C(O)NH$_2$, —NHN(H)NH$_2$, —NHC(O)NH$_2$, phenyl, indolyl or imidazolyl, said phenyl being optionally substituted with one, two, three or four groups independently selected from —OH, $C_1$-$C_6$-alkyl and —C(O)OH.

E23. The compounds of any one of E1 to E20, wherein $R^{10}$ is a 5- or 6-membered saturated heterocyclyl, optionally substituted with one, two, three or four groups independently selected from —OH, $C_1$-$C_6$-alkyl and —C(O)OH.

E24. The compounds of E23, wherein $R^{10}$ is pyrrolidinyl.

E25. The compounds of any one of E1 to E24, wherein $R^{10}$ is a residue of a natural amino acid and is derived from said amino acid by removal of a —COOH group.

E26. The compounds of E25, wherein said amino acid is an α-amino acid, i.e. an amino acid with a primary amino group at its C2 atom.

E27. The compounds of E26, wherein the residue of said amino acid is derived by removal of the —COOH group comprising the C1 atom of the amino acid.

E28. The compounds of any one of E1 to E14 and E16 to E18, wherein $R^8$ is —$C_1$-$C_6$-alkyl-C(O)NR$^{11}$—$R^{10}$, —$C_1$-$C_6$-alkyl-OC(O)NR$^{11}$—$R^{10}$ or —$C_1$-$C_6$-alkyl-NR$^{12}$C(O)NR$^{12}$—$R^{10}$.

E29. The compounds of E28, wherein $R^{10}$ is linear or branched $C_1$-$C_6$-alkyl substituted with one, two or three substituents independently selected from —NHR$^{13}$, —OH, —SR$^{13}$, —C(O)OH, —S(O)$_2$OH, —C(O)NH$_2$, —NHN(H)NH$_2$, —NHC(O)NH$_2$, $C_3$-$C_7$-cycloalkyl, aryl and 5- or 6-membered heteroaryl, said cycloalkyl, aryl and heteroaryl being optionally substituted with one, two, three or four substituents independently selected from —OH, $C_1$-$C_6$-alkyl and —C(O)OH.

E30. The compounds of E28, wherein $R^{10}$ is linear or branched $C_1$-$C_6$-alkyl substituted with one, two or three substituents independently selected from —NHR$^{13}$, —OH, —SR$^{13}$, —C(O)OH, —S(O)$_2$OH, —C(O)NH$_2$, —NHN(H)NH$_2$, —NHC(O)NH$_2$, phenyl, indolyl or imidazolyl, said phenyl being optionally substituted with one, two, three or four substituents independently selected from —OH, $C_1$-$C_6$-alkyl and —C(O)OH.

E31. The compounds of E28, wherein $R^{10}$ is 2-(1H-imidazol-5-yl)ethyl.

E32. The compounds of E28, wherein $R^{10}$ is a residue of an amino acid and derived from said amino acid by removal of a —NH$_2$ group.

E33. The compounds of E32, wherein said amino acid is an α-amino acid, i.e. an amino acid with a primary amino group at its C2 atom.

E34. The compounds of E33, wherein the residue of said amino acid is derived by removal of the —NH$_2$ group from the C2 atom of the amino acid.

E35. The compounds of any one of E25-E27 and E32-E34, wherein said amino acid is a naturally occurring amino acid.

E36. The compounds of any one of E25-E27 and E32-E34, wherein the amino acid is selected from isoleucine, alanine, leucine, asparagine, lysine, aspartic acid, methionine, cysteine, phenylalanine, histidine, tryptophan, glutamic acid, threonine, glutamine, glycine, valine, serine, tyrosine, arginine, proline, ornithine and citrulline.

E37. The compounds of E36, wherein the absolute stereoconfiguration at the C2 atom of the amino acid is L-configuration, i.e. the amino acid is an L-α-amino acid.

E38. The compounds of any one of E19, E20 or E28, wherein $R^{10}$ is —(CH$_2$CH$_2$O)$_m$H, —(CH(CH$_3$)CH$_2$O)$_m$H, or —(CH$_2$CH(CH$_3$)O)$_m$H, and m is 1 to 10.

E39. Examples of compounds of E1 include compounds of formulae

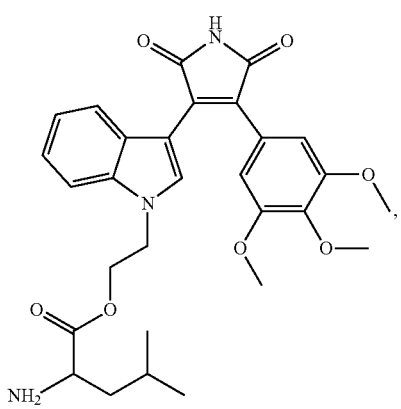

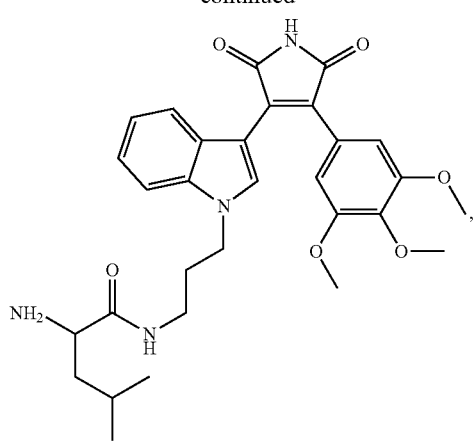

and the physiologically acceptable salts, solvates and solvates of the salts thereof.

E40. A pharmaceutical composition comprising at least one compound of formula I according to any one of E1-E39 and a pharmaceutically acceptable excipient, and, optionally, further comprising an additional chemotherapeutic agent.

E41. The composition of E40, wherein the additional chemotherapeutic agent is selected from antineoplastic agents, multidrug resistance reversing agents; and biological response modifiers, and combinations thereof.

E42. The composition of E40 or E41, wherein the chemotherapeutic agent is a topoisomerase I inhibitor, in particular selected from irinotecan, topotecan, rubitecan, exatecan, lurtotecan, gimatecan, prothecan, karenitecin, belotecan, silatecan and diflomotecan and the salts thereof.

E43. The composition of E42, wherein the topoisomerase I inhibitor is irinotecan or topotecan.

E44. A compound of formula I according to any one of E1 to E39 for use in treating tumors, optionally further comprising the use of an additional chemotherapeutic agent.

E45. The compound for use according to E44, wherein the additional chemotherapeutic agent is selected from antineoplastic agents, multidrug resistance reversing agents; and biological response modifiers, and combinations thereof.

E46. The compound for use according to E44, wherein the additional chemotherapeutic agent is a topoisomerase I inhibitor.

E47. The compound for use according to E46, wherein the topoisomerase I inhibitor is selected from irinotecan, topotecan, rubitecan, exatecan, lurtotecan, gimatecan, prothecan, karenitecin, belotecan, silatecan and diflomotecan and the salts thereof.

E48. The compound for use according to E46, wherein the topoisomerase I inhibitor is irinotecan or topotecan.

E49. A method of treating tumors in a mammal which comprises administering an effective amount of a compound of formula I according to any one of E1-E39 to a mammal in need of such treatment.

The invention claimed is:

1. 3-(Indolyl)- and 3-(azaindolyl)-4-phenylmaleimide compounds of formula I

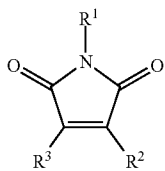

(I)

wherein
R$^1$ is —H, C$_1$-C$_6$-alkyl, phenyl-C$_1$-C$_4$-alkyl or phenyl;
R$^2$ is

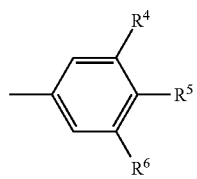

wherein R$^4$, R$^5$ and R$^6$ are C$_1$-C$_6$-alkoxy; and
R$^3$ is selected from:

a)
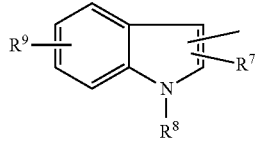

b)
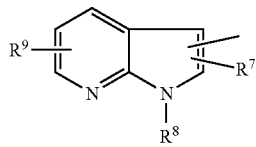

c)
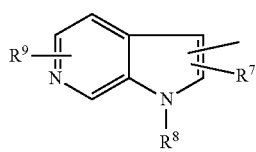

d)

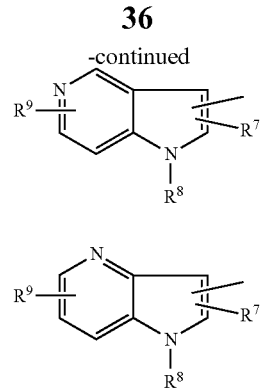

e)

wherein
R$^7$ is —H, C$_1$-C$_6$-alkyl or phenyl;
R$^9$ is —H, C$_1$-C$_6$-alkyl, C$_1$-C$_6$-alkoxy, —OH, halogen, —NH$_2$, C$_1$-C$_6$-alkylamino, di-C$_1$-C$_6$-alkylamino, heteroaryl with 5 or 6 ring atoms containing 1 or 2 heteroatoms which are independently selected from O, N, and S, or heterocyclyl with 5 or 6 ring atoms containing 1 or 2 heteroatoms which are independently selected from O, N, and S; and
R$^8$ is —C$_1$-C$_8$-alkyl-X$^1$—X$^2$—R$^{10}$, —C$_2$-C$_8$-alkenyl-X$^1$—X$^2$—R$^{10}$ or —C$_2$-C$_8$-alkynyl-X$^1$—X$^2$—R$^{10}$, wherein
X$^1$ is a single bond, —(OCH$_2$CH$_2$)$_n$—, or —(OCH$_2$CH$_2$CH$_2$)$_n$—, wherein n is 1, 2 or 3;
X$^2$ is —OC(O)—, —NR$^{11}$C(O)—, —C(O)O—, —C(O)NR$^{11}$—, —OC(O)NR$^{11}$—, —NR$^{11}$C(O)O—, —NR$^{12}$C(O)NR$^{12}$—, —OS(O)$_2$—, —S(O)$_2$O—, —OS(O)$_2$O—, —NR$^{11}$—, or

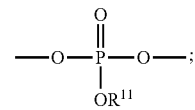

R$^{10}$ is selected from
a) linear or branched C$_1$-C$_6$-alkyl substituted with one substituent selected from —NHR$^{11}$, —OH, —SH, —C(O)OH and —S(O)$_2$OH, and optionally further substituted with one, two or three substituents independently selected from —NHR$^{13}$, —OH, —SR$^{13}$, —C(O)OH, —S(O)$_2$OH, —C(O)NH$_2$, —NHC(NH)NH$_2$, —NHC(O)NH$_2$, C$_3$-C$_7$-cycloalkyl, phenyl and 5- or 6-membered heteroaryl, said cycloalkyl being optionally substituted with one or two C$_1$-C$_6$-alkyl, and said phenyl and heterocyclyl being optionally substituted with one, two, three or four substituents independently selected from —OH, C$_1$-C$_6$-alkyl and —C(O)OH; or
b) a 5- or 6-membered saturated heterocyclyl, optionally substituted with one, two or three substituents independently selected from C$_1$-C$_6$-alkyl, —OH and —C(O)OH;
c) C$_1$-C$_6$-alkyl substituted with monocyclic or bicyclic heteroaryl, in particular with imidazolyl such as 5-imidazolyl, said aryl being optionally substituted with one, two, three or four substituents independently selected from —OH, C$_1$-C$_6$-alkyl and —C(O)OH;
d) monocyclic or bicyclic aryl, optionally substituted with one, two, three or four substituents independently selected from —OH, C$_1$-C$_6$-alkyl and —C(O)OH;

e) $C_3$-$C_7$-cycloalkyl optionally substituted with one or two $C_1$-$C_6$-alkyl;

f) monocyclic or bicyclic heteroaryl, optionally substituted with one, two, three or four substituents independently selected from —OH, $C_1$-$C_6$-alkyl, and —C(O)OH;

g) $C_1$-$C_6$-alkyl substituted with monocyclic or bicyclic aryl, in particular with phenyl, said aryl being optionally substituted with one, two or three substituents independently selected from —OH, $C_1$-$C_6$-alkyl, and —C(O)OH; and h) —$(CH_2CH_2O)_mH$, —$(CH(CH_3)CH_2O)_mH$, or —$(CH_2CH(CH_3)O)_mH$, wherein m is 1 to 10;

$R^{11}$ is selected from —H, $C_1$-$C_6$-alkyl, phenyl and benzyl;

$R^{12}$ is —H or $C_1$-$C_8$-alkyl; and $R^{13}$ is selected from —H, $C_1$-$C_6$-alkyl, phenyl and benzyl;

and the physiologically acceptable salts, solvates and solvates of the salts of the compounds of formula I.

2. The compounds of claim 1

(a) having formula Ia:

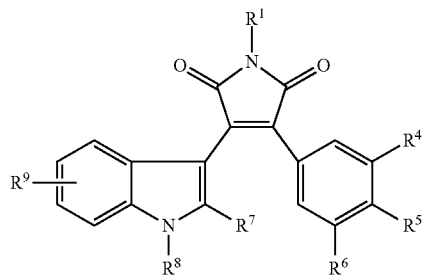

(Ia)

wherein $R^1$, $R^7$, $R^8$ and $R^9$ are as defined in claim 1 and $R^4$, $R^5$ and $R^6$ are $C_1$-$C_6$-alkoxy;

(b) having formula Ib:

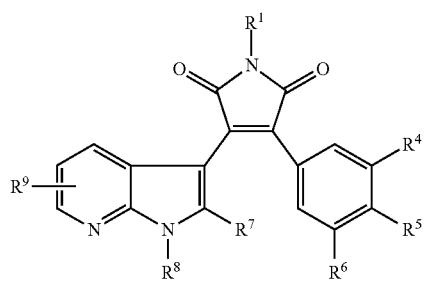

(Ib)

wherein $R^1$, $R^7$, $R^8$ and $R^9$ are as defined in claim 1 and $R^4$, $R^5$ and $R^6$ are $C_1$-$C_6$-alkoxy;

(c) having formula Ic:

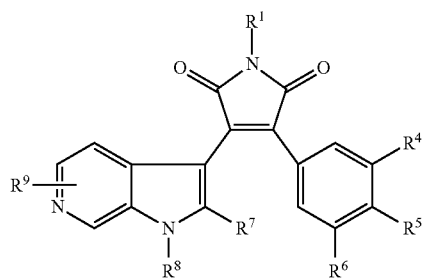

(Ic)

wherein $R^1$, $R^7$, $R^8$ and $R^9$ are as defined in claim 1 and $R^4$, $R^5$ and $R^6$ are $C_1$-$C_6$-alkoxy;

(d) having formula Id:

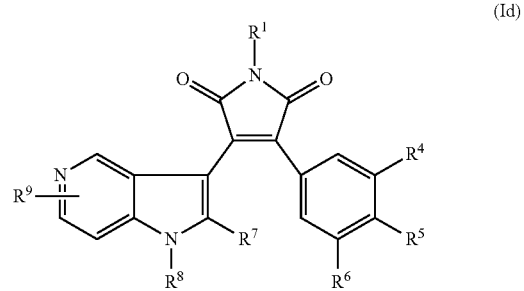

(Id)

wherein $R^1$, $R^7$, $R^8$ and $R^9$ are as defined in claim 1 and $R^4$, $R^5$ and $R^6$ are $C_1$-$C_6$-alkoxy; or (e) having formula Ie:

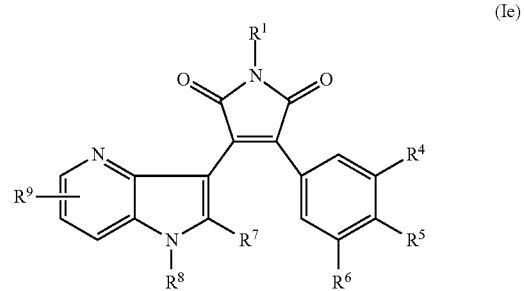

(Ie)

wherein $R^1$, $R^7$, $R^8$ and $R^9$ are as defined in claim 1 and $R^4$, $R^5$ and $R^6$ are $C_1$-$C_6$-alkoxy; and the physiologically acceptable salts, solvates and solvates of the salts of said compounds.

3. The compounds of claim 1, wherein $R^1$ and $R^7$ are —H, and $R^9$ is —H, $C_1$-$C_6$-alkyl or halogen; and the physiologically acceptable salts, solvates and solvates of the salts thereof.

4. The compounds of claim 1, wherein $R^8$ is —$C_1$-$C_8$-alkyl-$X^1$—OC(O)—$R^{10}$, —$C_1$-$C_8$-alkyl-$X^1$—$NR^{11}$C(O)—$R^{10}$, —$C_1$-$C_8$-alkyl-$X^1$—C(O)$NR^{11}$—$R^{10}$, —$C_1$-$C_8$-alkyl-$X^1$—OC(O)$NR^{11}$—$R^{10}$ or —$C_1$-$C_8$-alkyl-$X^1$—$NR^{12}$C(O)$NR^{12}$—$R^{10}$; and the physiologically acceptable salts, solvates and solvates of the salts thereof.

5. The compounds of claim 1, wherein $R^{10}$ is selected from a) linear or branched $C_1$-$C_6$-alkyl substituted with one residue selected from —$NHR^{11}$, —OH, —SH and —C(O)OH, and optionally further substituted with one, two or three residues independently selected from —$NHR^{13}$, —OH, —$SR^{13}$, —C(O)OH, —C(O)$NH_2$, —NHC(NH)$NH_2$, —NHC(O)$NH_2$, phenyl, hydroxyphenyl, indolyl and imidazolyl, said indolyl or imidazolyl being optionally substituted with one, two, three or four substituents independently selected from —OH, $C_1$-$C_6$-alkyl and —C(O)OH;

b) 5- or 6-membered saturated heterocycloalkyl, optionally substituted with one or two substituents independently selected from $C_1$-$C_6$-alkyl, —OH and —C(O)OH; and c) $C_1$-$C_6$-alkyl substituted with imidazolyl; and the physiologically acceptable salts, solvates and solvates of the salts thereof.

6. The compounds of claim 1, wherein $R^{10}$ is 2-(1H-imidazol-5-yl)ethyl, or a residue of an amino acid that is derived from said amino acid by removal of an —COOH, —$NH_2$ or —OH group; and the physiologically acceptable salts, solvates and solvates of the salts thereof.

7. The compounds of claim 6, wherein the amino acid is selected from isoleucine, alanine, leucine, asparagine, lysine, aspartic acid, methionine, cysteine, phenylalanine, histidine, tryptophan, glutamic acid, threonine, glutamine, glycine, valine, serine, tyrosine, arginine, proline, ornithine and citrulline; and the physiologically acceptable salts, solvates and solvates of the salts thereof.

8. The compounds of claim 6, wherein said amino acid is an α-amino acid; and the physiologically acceptable salts, solvates and solvates of the salts thereof.

9. The compounds of claim 6, wherein the residue is derived from said amino acid by removal of the —COOH group comprising the C1 atom of the amino acid; and the physiologically acceptable salts, solvates and solvates of the salts thereof.

10. The compounds of claim 6, wherein the residue is derived from said amino acid by removal of the —NH₂ group from the C2 atom of the amino acid; and the physiologically acceptable salts, solvates and solvates of the salts thereof.

11. The compounds of claim 6, wherein the absolute stereoconfiguration at the C2 atom of the amino acid is L-configuration; and the physiologically acceptable salts, solvates and solvates of the salts thereof.

12. The compounds of claim 1 having a formula selected from

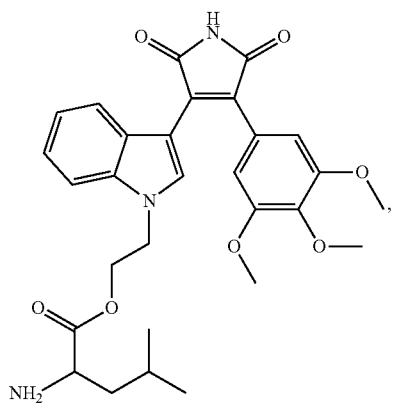

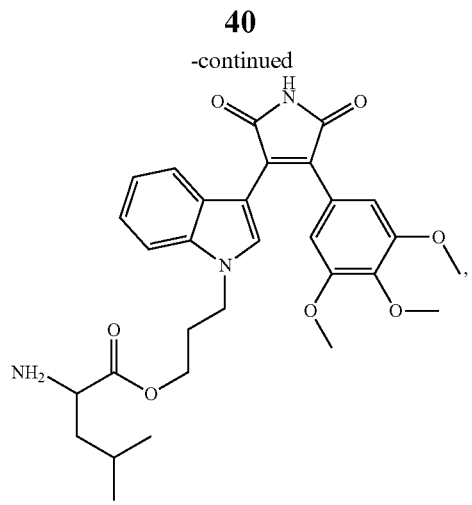

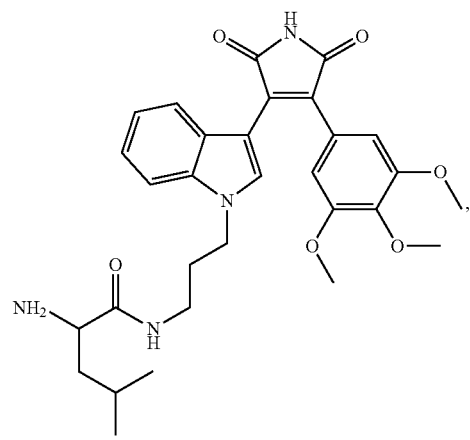

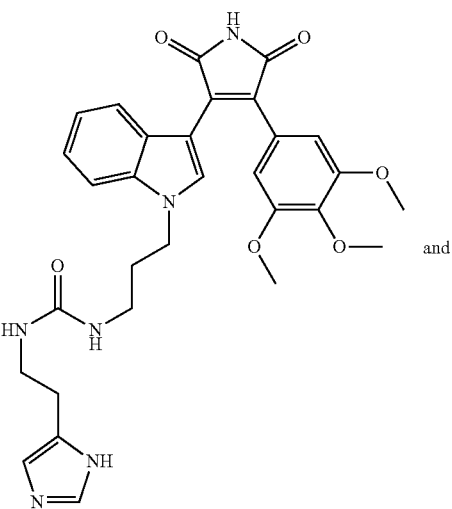

and

-continued

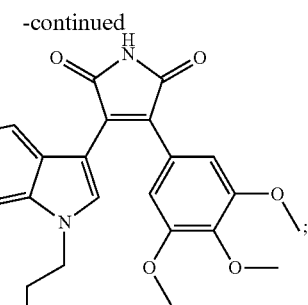

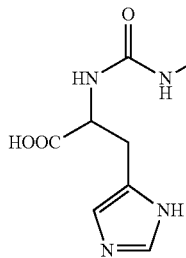

and the physiologically acceptable salts, solvates and solvates of the salts thereof.

13. A pharmaceutical composition comprising at least one compound of formula I according to claim 1, and the physiologically acceptable salts, solvates and solvates of the salts of the compounds of formula I and a pharmaceutically acceptable excipient, and, optionally, further comprising an additional chemotherapeutic agent.

14. The composition of claim 13, wherein the additional chemotherapeutic agent is selected from antineoplastic agents, multidrug resistance reversing agents; and biological response modifiers, and combinations thereof.

15. A method of treating tumors comprising administering a compound of formula I according to claim 1 and the physiologically acceptable salts, solvates and solvates of the salts of the compounds of formula I.

16. The method of claim 15 further comprising administering an additional chemotherapeutic agent.

* * * * *